(12) United States Patent
Magee

(10) Patent No.: US 6,756,392 B2
(45) Date of Patent: Jun. 29, 2004

(54) NICOTINAMIDE DERIVATIVES USEFUL AS PDE4 INHIBITORS

(75) Inventor: Thomas V. Magee, Mystic, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/361,083

(22) Filed: Feb. 6, 2003

(65) Prior Publication Data

US 2003/0195233 A1 Oct. 16, 2003

Related U.S. Application Data

(60) Provisional application No. 60/362,154, filed on Mar. 5, 2002.

(30) Foreign Application Priority Data

Feb. 11, 2002 (GB) .............................................. 0203193

(51) Int. Cl.[7] ........................ A61K 31/44; C07D 213/64
(52) U.S. Cl. ........................ 514/350; 546/298; 546/296; 546/291; 546/290; 546/304; 514/346; 514/348; 514/352
(58) Field of Search ................................ 514/350, 348, 514/346, 352; 546/298, 296, 291, 290, 304

(56) References Cited

FOREIGN PATENT DOCUMENTS

| WO | WO 9111172 | 8/1991 | ............ A61K/9/00 |
|---|---|---|---|
| WO | WO 9402518 | 2/1994 | ............ C08B/37/16 |
| WO | WO 9845268 | 10/1998 | ......... C07D/213/82 |
| WO | WO 9855148 | 12/1998 | ........... A61K/47/48 |
| WO | WO 0157036 | 8/2001 | ......... C07D/413/12 |

OTHER PUBLICATIONS

Torphy et al., Environ. Health Perspect., 1994, 102, Suppl. 10, 79–84.
Duplantier et al., J. Med. Chem., 1996, 39, p. 120–125.
Schneider et al., Pharmacol. Biochem. Behav., 1995. 50. p 211–217.
Banner and Page, Br. J. Pharmacol., 1995, 114, p. 93–98.
Barnette et al., J. Pharmacol. Exp. Ther., 1995, 273, p. 674–679.
Wright et al., Can. J. Physiol. Pharmacol,, 1997, 75, p. 1001–1008.
Manabe et al., Eur J. Pharmacol, 1997, 332, 97–107.
Ukita et al., J. Med. Chem., 1999, 42, p. 1088–1099.
Berge et al., J. Pharm. Sci, 1977, 66, p. 1–19.

*Primary Examiner*—Charanjit S. Aulakh
(74) *Attorney, Agent, or Firm*—Peter C. Richardson; Gregg C. Benson; Robert T. Ronau

(57) ABSTRACT

The invention relates to nicotinamide derivatives and to processes for the preparation of, intermediates used in the preparation of, compositions containing and the uses of, such derivatives. The nicotinamide derivatives according to the present invention are useful in numerous diseases, disorders and conditions, in particular inflammatory, allergic and respiratory diseases, disorders and conditions as well as for wounds healing.

20 Claims, No Drawings

NICOTINAMIDE DERIVATIVES USEFUL AS PDE4 INHIBITORS

CROSS REFERENCE TO RELATED APLICATIONS

This application claims the benefit of U.S. Provisional United States of America Application No. 60/362,154 filed 5 Mar. 2002. This application also claims the benefit of United Kingdom Application No. 0203193.8 flled 11 Feb. 2002.

This invention relates to nicotinamide derivatives of general formula:

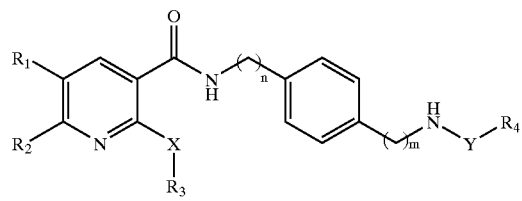

(1)

in which $R_1$, $R_2$, $R_3$, $R_4$, X, Y, n and m have the meanings indicated below, and to processes for the preparation of, intermediates used in the preparation of, compositions containing and the uses of, such derivatives.

The 3',5'-cyclic nucleotide phosphodiesterases (PDEs) comprise a large class of enzymes divided into at least eleven different families which are structurally, biochemically and pharmacologically distinct from one another. The enzymes within each family are commonly referred to as isoenzymes, or isozymes. A total of more than fifteen gene products is included within this class, and further diversity results from differential splicing and post-translational processing of those gene products. The present invention is primarily concerned with the four gene products of the fourth family of PDEs, i.e., PDE4A, PDE4B, PDE4C, and PDE4D. These enzymes are collectively referred to as being isoforms or subtypes of the PDE4 isozyme family.

The PDE4s are characterized by selective, high affinity hydrolytic degradation of the second messenger cyclic nucleotide, adenosine 3',5'-cyclic monophosphate (cAMP), and by sensitivity to inhibition by rolipram. A number of selective inhibitors of the PDE4s have been discovered in recent years, and beneficial pharmacological effects resulting from that inhibition have been shown in a variety of disease models (see, e.g., Torphy et al., *Environ. Health Perspect.*, 1994, 102 Suppl. 10, p. 79–84; Duplantier et al., *J. Med. Chem.*, 1996, 39, p. 120–125; Schneider et al., *Pharmacol. Biochem. Behav.,* 1995, 50, p. 211–217; Banner and Page, *Br. J. Pharmacol.,* 1995, 114, p. 93–98; Barnette et al., *J. Pharmacol. Exp. Ther.,* 1995, 273, p. 674–679; Wright et al., *Can. J. Physiol. Pharmacol.,* 1997, 75, p. 1001–1008; Manabe et al.,*Eur. J. Pharmacol.,* 1997, 332, p. 97–107 and Ukita et al., *J. Med. Chem.,* 1999, 42, p. 1088–1099). Accordingly, there continues to be considerable interest in the art with regard to the discovery of further selective inhibitors of PDE4s.

Successful results have already been obtained in the art with the discovery and development of selective PDE4 inhibitors. In vivo, PDE4 inhibitors reduce the influx of eosinophils to the lungs of allergen-challenged animals while also reducing the bronchoconstriction and elevated bronchial responsiveness occurring after allergen challenge. PDE4 inhibitors also suppress the activity of immune cells (including CD4$^+$ T-lymphocytes, monocytes, mast cells, and basophils), reduce pulmonary edema, inhibit excitatory nonadrenergic noncholinergic neurotransmission (eNANC), potentiate inhibitory nonadrenergic noncholinergic neurotransmission (iNANC), reduce airway smooth muscle mitogenesis, and induce bronchodilation. PDE4 inhibitors also suppress the activity of a number of inflammatory cells associated with the pathophysiology of COPD, including monocytes/macrophages, CD4$^+$ T-lymphocytes, eosinophils and neutrophils. PDE4 inhibitors also reduce vascular smooth muscle mitogenesis and potentially interfere with the ability of airway epithelial cells to generate pro-inflammatory mediators. Through the release of neutral proteases and acid hydrolases from their granules, and the generation of reactive oxygen species, neutrophils contribute to the tissue destruction associated with chronic inflammation, and are further implicated in the pathology of conditions such as emphysema. Therefore, PDE4 inhibitors are particularly useful for the treatment of a great number of inflammatory, respiratory and allergic diseases, disorders or conditions, as well as for wounds and some of them are in clinical development mainly for treatment of asthma, COPD, bronchitis and emphysema.

The effects of PDE4 inhibitors on various inflammatory cell responses can be used as a basis for profiling and selecting inhibitors for further study. These effects include elevation of cAMP and inhibition of superoxide production, degranulation, chemotaxis, and tumor necrosis factor alpha (TNF□) release in eosinophils, neutrophils and monocytes.

As said above, the present invention relates to PDE4 inhibitors of the nicotinamide derivatives family.

Nicotinamide derivatives having a PDE4 inhibitory activity have already been synthetized. For example, the patent application No WO 98/45268 discloses nicotinamide derivatives having activity as selective inhibitors of PDE4D isozyme. These selective PDE4D inhibitors are represented by the following formula:

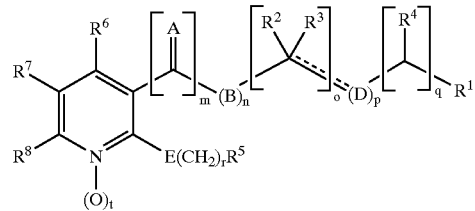

wherein in particular m and n may be equal to 1 and p may be equal to 0, A may be oxygen, B may be NH, r may be equal to 0, E may be O, NH or S, $R^5$ may be a saturated or unsaturated cyclic or bicyclic ($C_3$–$C_7$)heterocyclic group containing 1 to 4 heteroatoms and $R^1$ may be an aryl optionally substituted by various substituents.

Also, the patent application No WO 01/57036 also discloses nicotinamide derivatives which are PDE4 inhibitors useful in the treatment of various inflammatory allergic and respiratory diseases and conditions, of formula wherein in particular: n is 1 or 2, m is 0 to 2, Y is =C($R^E$)— or —[N→(O)]—, W is —O—, —S(=O)$_t$— or —N(R$_3$)—, Q represents various rings among which phenyl, Z is —OR$_{12}$, —C(=O)R$_{12}$ or CN and R$_{12}$ is choosen from alkyl, alkenyl, cycloalkyl, phenyl, benzyl and monocyclic heterocyclic moieties.

However, there is still a huge need for additional PDE4 inhibitors showing improved therapeutic index with possibly less adverse effects such as for example emesis.

Thus, the present invention concerns new nicotinamide derivatives of general formula (1):

(1)

in which:

m is 0, 1, 2 or 3, n is 0, 1, 2 or 3,

R$_1$ and R$_2$ are each a member independently selected from the group consisting of hydrogen atom, halo, cyano, (C$_1$-C$_4$)alkyl and (C$_1$-C$_4$)alkoxy, X is —O—, —S— or —NH—, R$_3$ is a member selected from the groups consisting of:
(a) phenyl, naphthyl, heteroaryl and (C$_3$-C$_8$) cycloalkyl, each optionally substituted with 1 to 3 substituents each selected from the group consisting of halo, cyano, (C$_1$-C$_4$)alkyl, (C$_1$-C$_4$)alkoxy, (C$_1$-C$_4$)thioalkyl, —C(=O)NH$_2$, —C(=O)NH ((C$_1$-C$_4$)alkyl), hydroxy, —O—C(=O)(C$_1$-C$_4$) alkyl, —C(=O)—O—(C$_1$-C$_4$)alkyl and hydroxy (C$_1$-C$_4$)alkyl, or
(b) the bicyclic groups conforming to one of the following structures (1.1) to (1.4):

(1.1)

(1.2)

(1.3)

(1.4)

where the symbol "*" indicates the point of attachment of each partial formula (1.1) through (1.4) to the remaining portion of formula (1), Y is a member selected from the group consisting of partial formulas (1.5) through (1.11):

(1.5)

(1.6)

(1.7)

(1.8)

(1.9)

(1.10)

(1.11)

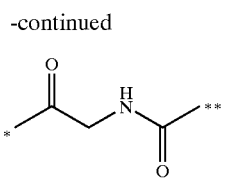

where the symbol "*" indicates the point of attachment of each partial formula (1.5) through (1.11) to the remaining portions —NH— of formula (1) and "**" indicates the point of attachment of each partial formula (1.5) through (1.11) to the remaining portions —$R_4$ of formula (1), and $R_4$ is a member selected from the groups consisting of:
(a) phenyl, naphthyl and heteroaryl, each optionally substituted with 1 to 3 substituents each selected from the group consisting of carboxylic acid, C(=O)—O—($C_1$–$C_4$)alkyl, halo, cyano, —C(=O)$NH_2$, ($C_1$–$C_4$)alkyl, ($C_1$–$C_4$)alkoxy, ($C_1$–$C_4$)haloalkyl, hydroxy, and hydroxy($C_1$–$C_4$)alkyl, or
(b) ($C_1$–$C_4$)alkyl optionally substituted with a hydroxy, carboxylic acid, C(=O)—O—($C_1$–$C_4$)alkyl, phenyl, naphthyl or heteroaryl group wherein said phenyl, naphthyl and heteroaryl are each optionally substituted with 1 to 3 substituents each selected from the group consisting of carboxylic acid, C(=O)O($C_1$–$C_4$)alkyl, halo, cyano, —C(=O)$NH_2$, ($C_1$–$C_4$)alkyl or ($C_1$–$C_4$)alkoxy, ($C_1$–$C_4$)haloalkyl, hydroxy, and hydroxy($C_1$–$C_4$)alkyl, or, if appropriate, their pharmaceutically acceptable salts and/or isomers, tautomers, solvates, polymorphs, isotopic variations or metabolites thereof.

It has been found that these nicotinamide derivatives are inhibitors of PDE4 isoenzymes, particularly useful for the treatment of inflammatory, respiratory and allergic diseases and conditions and for the treatment of wounds by showing excellent therapeutic utility and therapeutic index.

In the here above general formula (1), halo denotes a halogen atom selected from the group consisting of fluoro, chloro, bromo and iodo in particular fluoro or chloro.

($C_1$–$C_4$)alkyl radicals denote a straight-chain or branched group containing 1, 2, 3 or 4 carbon atoms. This also applies if they carry substituents or occur as substituents of other radicals, for example in ($C_1$–$C_4$)alkoxy radicals, ($C_1$–$C_4$)thioalkyl radicals, ($C_1$–$C_4$)haloalkyl radicals, hydroxy ($C_1$–$C_4$)alkyl radicals, C(=O)O($C_1$–$C_4$)alkyl radicals etc. . . . Examples of suitable ($C_1$–$C_4$)alkyl radicals are methyl, ethyl, n-propyl, iso-propyl, n-butyl, iso-butyl, sec-butyl and tert-butyl. Examples of suitable ($C_1$–$C_4$)alkoxy radicals are methoxy, ethoxy, n-propyloxy, iso-propyloxy, n-butyloxy, iso-butyloxy, sec-butyloxy and tert-butyloxy. Examples of suitable ($C_1$–$C_4$)thioalkyl radicals are thiomethyl, thioethyl, thio-n-propyl, thio-iso-propyl, thio-n-butyl, thio-iso-butyl, thio-sec-butyl and thio-tert-butyl. ($C_1$–$C_4$)haloalkyl radicals are alkyl radicals substituted by halo. They can contain 1, 2, 3, 4, 5, 6 or 7 halogen atoms, if not stated otherwise. Said halo is preferably a fluoro, a chloro, a bromo or a iodo, in particular fluoro or chloro. For example in a fluoro-substituted alkyl radical, a methyl group can be present as a trifluoromethyl group. The same applies to hydroxy($C_1$–$C_4$)alkyl radicals except that they are alkyl radicals substituted by a hydroxy group (—OH). According to a preferred embodiment of said invention, such radicals contain one hydroxy substituent. Examples of suitable hydroxy($C_1$–$C_4$)alkyl radicals are hydroxymethyl, 1-hydroxyethyl or 2-hydroxyethyl.

($C_3$–$C_8$)cycloalkyl radicals represent 3-membered to 8-membered saturated monocyclic rings. Examples of suitable ($C_3$–$C_8$)cycloalkyl radicals are in particular cyclopropyl, cyclobutyl, cyclopentyl, cyclohexyl, cycloheptyl and cyclooctyl. These radicasl can be optionally substituted as indicated in the definition of $R_3$. Examples of substituted ($C_3$–$C_8$)cycloalkyl radicals are 2-methylcyclohexyl, 3-methylcyclohexyl, 4-methylcyclohexyl, 5-methylcyclohexyl, 6-methylcyclohexyl, 2-hydroxycyclohexyl, 3-hydroxycyclohexyl, 4-hydroxycyclohexyl, 5-hydroxycyclohexyl, 6-hydroxycyclohexyl, 2-fluorocyclohexyl, 3-fluorocyclohexyl, 4-fluorocyclohexyl, 5-fluorocyclohexyl, 6-fluorocyclohexyl 2-methyl-3-hydroxycyclohexyl, 2-methyl-4-hydroxycyclohexyl, 2-hydroxy-4-methylcyclohexyl, etc. . . .

In the hereabove general formula (1), heteroaryl is a radical of a monocyclic or polycyclic aromatic system having 5 to 14 ring members, which contains 1, 2, 3, 4 or 5 heteroatom(s) depending in number and quality of the total number of ring members. Examples of heteroatoms are nitrogen (N), oxygen (O) and sulphur (S). If several heteroatoms are contained, these can be identical or different. Heteroaryl radicals can also be unsubstituted, monosubstituted or polysubstituted, as indicated in the definition of $R_3$ and $R_4$ hereabove for general formula (1) according to the present invention. Preferably the heteroaryl is a monocyclic or bicyclic aromatic radical which contains 1, 2, 3 or 4, in particular 1, 2 or 3, identical or different heteroatoms selected from the group consisting of N, O and S. Particularly preferably, the heteroaryl is a monocyclic or bicyclic aromatic radical having 5 to 10 ring members, in particular a 5-membered to 6-membered monocyclic aromatic radical which contains (i) from 1 to 4 nitrogen heteroatom(s) or (ii) 1 or 2 nitrogen heteroatom(s) and 1 oxygen heteroatom or 1 sulphur heteroatom or (iii) 1 or 2 oxygen or sulphur heteroatom(s). Examples of suitable heteroaryl radicals are the radicals derived from pyrrole, furan, furazan, thiophene, imidazole, pyrazole, oxazole, isoxazole, thiazole, isothiazole, tetrazole, triazine, pyridine, pyrazine, pyrimidine, pyridazine, indolizine, indole, isoindole, indazole, purine, naphtyridine, phthalazine, quinoline, isoquinoline, quinoxaline, quinazoline, cinnoline, and benzo-fused derivatives of these heteroaryls, such as for example benzofuran, benzothiophene, benzoxazole, and benzothiazole. Particularly preferred are the heteroaryl radicals selected from pyrrolyl, pyrazolyl, 1,2,3-triazolyl, 1,2,4-triazolyl, tetrazolyl, oxazolyl, isoxazolyl, thiazolyl, isothiazolyl, 1,2,4-oxadiazolyl, 1,3,4-oxadiazolyl, furanyl, thienyl, pyridinyl, pyridazinyl, pyrimidinyl, and pyrazinyl. Nitrogen heteroaryl radicals can also be present as N-oxides or as quaternary salts.

In the general formula (1) according to the present invention, when a radical is mono- or poly-substituted, said substituent(s) can be located at any desired position(s). Also, when a radical is polysubstituted, said substituents can be identical or different.

The nicotinamide derivatives of the formula (1) can be prepared using conventional procedures such as by the following illustrative methods in which $R_1$, $R_2$, $R_3$, $R_4$, X, Y, n and m are as previously defined for the nicotinamide derivatives of the formula (1) unless otherwise stated.

The nicotinamide derivatives of the formula (1) may be prepared starting from a compound of formula (2):

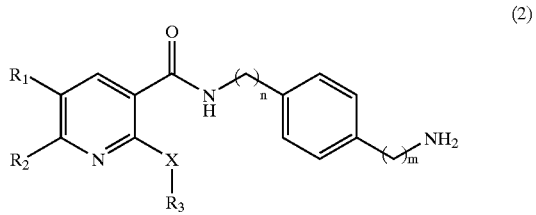

(2)

wherein $R_1$, $R_2$, X, $R_3$, n and m are as previously described for the nicotinamide derivatives of formula (1).

Where Y represents a group of partial formula (1.7), (1.8) or (1.10), the compounds of formula (2) may be reacted with the corresponding $R_4$-sulfonyl chloride derivative ($R_4SO_2Cl$ or $R_4NHSO_2Cl$ or $R_4C(=O)NHSO_2Cl$) in a suitable solvent (e.g. dichloromethane) and in the presence of an organic base (e.g. triethylamine) at a temperature ranging from 0° C. to room temperature (about 20° C.).

Where Y represents a group of partial formula (1.5), (1.9) or (1.11), the compounds of formula (2) may be reacted with the corresponding $R_4$-carboxylic acid derivative ($R_4COOH$ or $R_4SO_2NH-CH_2-COOH$ or $R_4C(O)NH-CH_2-COOH$) using an activating agent in the presence of a suitable solvent (e.g. dimethylformamide) and organic base (e.g. N-methylmorpholine) at room temperature. Activation of the acid may be achieved by using for example:

a) 1-hydroxybenzotriazole and 1-(3-dimethylaminopropyl)-3-ethylcarbodiimide hydrochloride,
b) carbonyldiimidazole, or
c) oxalyl chloride and dimethylformamide (with dichloromethane as the solvent).

Where Y represents a group of partial formula (1.6), the compounds of formula (2) may be reacted with carbonyldiimidazole in a suitable solvent (such as dichloromethane) and the obtained intermediate is reacted with an amine bearing the substituent $R_4$.

It must be emphasized that where $R_3$ and $R_4$ in the nicotinamide derivatives of formula (1) represent alkoxy substituted phenyl rings, these structures can be converted to the hydroxy analogue using certain deprotection conditions well-known to the one skilled in the art.

The compounds of general formula (2) may be prepared by removal of the protecting group "Prot" from the compounds of general formula (3):

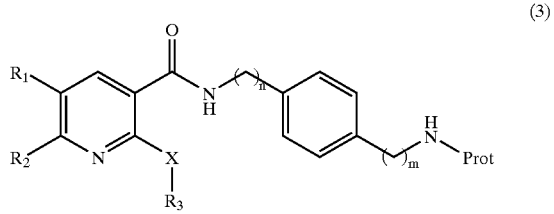

(3)

wherein $R_1$, $R_2$, X, $R_3$, n and m are as previously described for the nicotinamide derivatives of formula (1) and Prot is a suitable protecting group, which includes but is not limited to a benzyl group, a carbamate (e.g. tert-butyloxycarbonyl), an amide (e.g. trifluoroacetamide) or an imide (e.g. phtalimide), using deprotection conditions well-known to the one skilled in the art.

The compounds of formula (3) may be prepared as shown in scheme 1:

Scheme 1

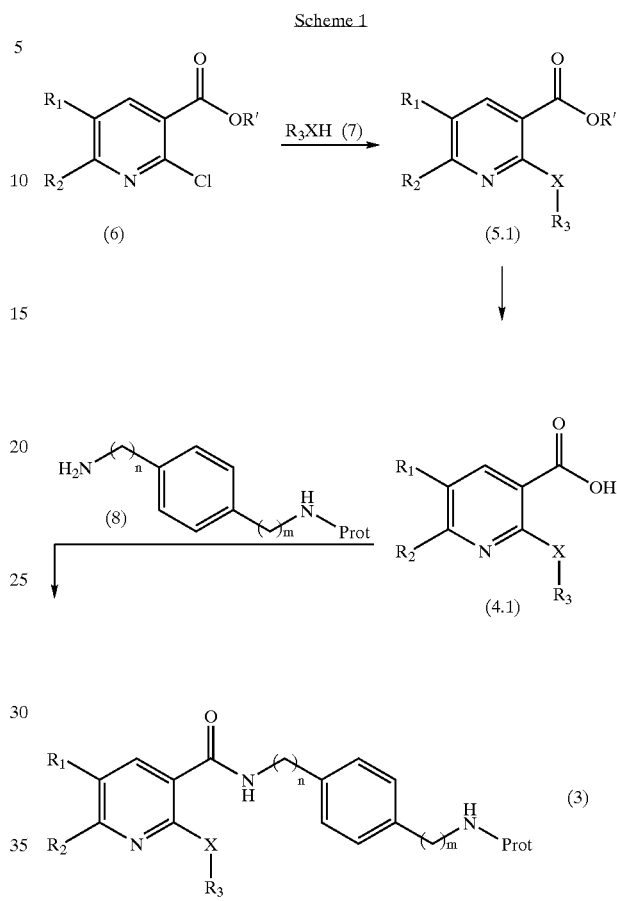

wherein $R_1$, $R_2$, X, $R_3$, n, m and Prot are as previously described and R' represents a ($C_1$–$C_4$)alkyl radical.

In a typical procedure the nicotinate ester of the formula (6) may be reacted with the appropriate alcohol, thiol or amine of formula $R_3XH$ (7) in the appropriate solvent (for example dimethylformamide or dioxan) containing a base, such as cesium carbonate, at temperatures ranging from room temperature to 100° C. to give a compound of the formula (5.1). This can be saponified with an alkalihydroxide to give an acid of the formula (4.1) which is then converted to a compound of the formula (3) by reaction with a monoprotected diamine of the formula (8):

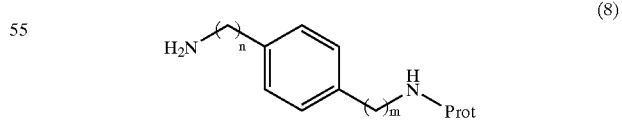

(8)

using an activating agent such as those described in one of the activation methods outlined before (i.e. a) 1-hydroxybenzotriazole and 1-(3-dimethylaminopropyl)-3-ethylcarbodiimide hydrochloride or b) carbonyldiimidazole or c) oxalyl chloride and dimethylformamide, with dichloromethane as the solvent).

According to another alternative, the compounds of formula (3) may be prepared as shown in scheme 2:

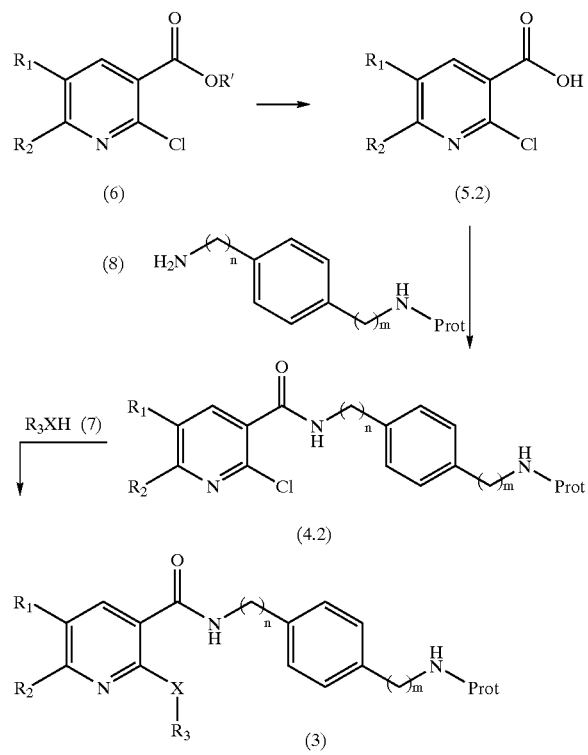

wherein $R_1$, $R_2$, X, $R_3$, n, m, R' and Prot are as previously described.

In a typical procedure the nicotinate ester of the formula (6) may be hydrolysed using an alkaline metal hydroxide to a nicotinic acid of the formula (5.2), which is reacted with a monoprotected diamine of the formula (8) using one of the activation methods outlined before. The chloropyridine of the formula (4.2) obtained at the preceding step may be reacted with the appropriate alcohol, thiol or amine of formula $R_3XH$ (7) in the appropriate solvent (for example dimethylformamide or dioxan) containing a base, such as cesium carbonate, at temperatures ranging from room temperature to 100° C.

The compounds of formula (6) and (7) are either commercial or they can be prepared by conventional procedures well known to the one skilled in the art.

The monoprotected diamine of the formula (8) may be prepared by reaction of a large excess of a diamine of formula (9):

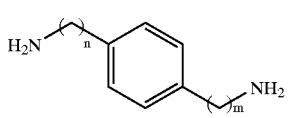

(9)

wherein m and n are as defined above, with a suitable derivatizing agent such as di-tert-butyldicarboxylate (to give the tert-butyloxycarbonyl derivative) at room temperature in a suitable solvent (such as dichloromethane).

The compounds of formula (9) are commercial or they can be easily prepared by conventional procedures well known to the one skilled in the art.

All of the above reactions and the preparations of novel starting materials using in the preceding methods are conventional and appropriate reagents and reaction conditions for their performance or preparation as well as procedures for isolating the desired products will be well-known to those skilled in the art with reference to literature precedents and the examples and preparations hereto.

For some of the steps of the here above described process of preparation of the nicotinamide derivatives of formula (1), it can be necessary to protect the potential reactive functions that are not wished to react. In such a case, any compatible protecting radical can be used. In particular methods such as those described by T. W. GREENE (*Protective Groups in Organic Synthesis*, A. Wiley-Interscience Publication, 1981) or by McOMIE (*Protective Groups in Organic Chemistry*, Plenum Press, 1973), can be used.

Also, the nicotinamide derivatives of formula (1) as well as intermediate for the preparation thereof can be purified according to various well-known methods, such as for example crystallization or chromatography.

According to a general aspect of the present invention, the nicotinamide derivatives of the formula (1) as previously described except the compounds for which 1) m is different from 0 simultaneously with Y representing the partial formula (1.5) and $R_4$ representing a non-substituted ($C_1$–$C_4$)alkyl,
2) m is equal to 0 simultaneously with Y representing the partial formula (1.5) and $R_4$ representing a phenyl, a naphtyl or a heteroaryl each optionally substituted with 1 to 3 substituents independently selected from the group consisting of carboxylic acid, halo, cyano, ($C_1$–$C_4$)alkyl, ($C_1$–$C_4$)alkoxy, ($C_1$–$C_4$)haloalkyl, hydroxy and hydroxy($C_1$–$C_4$)alkyl or $R_4$ representing a ($C_1$–$C_4$)alkyl optionally substituted with a hydroxy, carboxylic acid, or a heteroaryl, which is optionally substituted with 1 to 3 substituents independently selected from the group consisting of carboxylic acid, halo, cyano, ($C_1$–$C_4$)alkyl, ($C_1$–$C_4$)alkoxy, hydroxy and hydroxy($C_1$–$C_4$)alkyl, and
3) m is equal to 0 simultaneously with Y representing the partial formula (1.6) and $R_4$ representing a phenyl or a naphtyl, each optionally substituted with 1 to 3 substituents independently selected from the group consisting of carboxylic acid, halo, cyano, ($C_1$–$C_4$)alkyl, ($C_1$–$C_4$)alkoxy, ($C_1$–$C_4$)haloalkyl, hydroxy and hydroxy($C_1$–$C_4$)alkyl, are preferred.

Particularly preferred are nicotinamide derivatives of the formula (1) in which:

m and n are equal to 1, $R_1$ and $R_2$ are each a member independently selected from the group consisting of hydrogen atom, halo, cyano, ($C_1$–$C_4$)alkyl and ($C_1$–$C_4$)alkoxy, X is —O—, $R_3$ is a member selected from the groups consisting of:
(a) phenyl, naphthyl, heteroaryl and ($C_3$–$C_8$) cycloalkyl, each optionally substituted with 1 to 3 substituents each selected from the group consisting of halo, cyano, ($C_1$–$C_4$)alkyl, ($C_1$–$C_4$)alkoxy, ($C_1$–$C_4$)thioalkyl, —C(=O)$NH_2$, —C(=O)NH (($C_1$–$C_4$)alkyl), hydroxy, —O—C(=O)($C_1$–$C_4$) alkyl, —C(=O)—O—($C_1$–$C_4$)alkyl and hydroxy ($C_1$–$C_4$)alkyl, or
(b) the bicyclic groups conforming to one of the following structures (1.1) to (1.4):

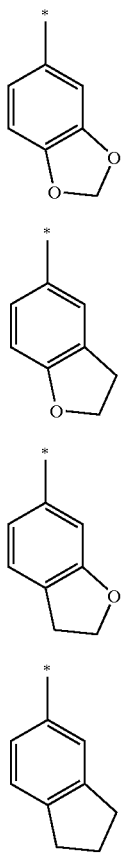

(1.1)

(1.2)

(1.3)

(1.4)

where the symbol "*" indicates the point of attachment of each partial formula (1.1) through (1.4) to the remaining portion of formula (1), Y is a group —C(=O)— of partial formula (1.5)
and $R_4$ is a member selected from the groups consisting of:
(a) phenyl, naphthyl and heteroaryl, each optionally substituted with 1 to 3 substituents each selected from the group consisting of carboxylic acid, C(=O)—O—($C_1$-$C_4$)alkyl, halo, cyano, —C(=O)NH$_2$, ($C_1$-$C_4$)alkyl, ($C_1$-$C_4$)alkoxy, ($C_1$-$C_4$)haloalkyl, hydroxy, and hydroxy($C_1$-$C_4$)alkyl, or
(b) ($C_1$-$C_4$)alkyl substituted with a hydroxy, carboxylic acid, C(=O)—O—($C_1$-$C_4$)alkyl, phenyl, naphthyl or heteroaryl group wherein said phenyl, naphthyl and heteroaryl are each optionally substituted with 1 to 3 substituents each selected from the group consisting of carboxylic acid, C(=O)O($C_1$-$C_4$)alkyl, halo, cyano, —C(=O)NH$_2$, ($C_1$-$C_4$)alkyl, ($C_1$-$C_4$)alkoxy, ($C_1$-$C_4$)haloalkyl, hydroxy, and hydroxy ($C_1$-$C_4$)alkyl, or, if appropriate, their pharmaceutically acceptable salts and/or isomers, tautomers, solvates, polymorphs, isotopic variations or metabolites thereof.

More particularly preferred are the nicotinamide derivatives of the formula (1) in which:
m and n are equal to 1,
$R_1$ and $R_2$ are each a member independently selected from the group consisting of hydrogen atom, halo and methyl,
X is —O—,
$R_3$ is a phenyl optionally substituted with 1 to 3 substituents each selected from the group consisting of halo, cyano, ($C_1$-$C_4$)alkyl, ($C_1$-$C_4$)alkoxy, ($C_1$-$C_4$) thioalkyl, —C(=O)NH$_2$, —C(=O)NH(($C_1$-$C_4$) alkyl), hydroxy, —O—C(=O)($C_1$-$C_4$)alkyl, —C(=O)—O—($C_1$-$C_4$)alkyl and hydroxy($C_1$-$C_4$) alkyl, Y is a group —C(=O)— of partial formula (1.5)
and $R_4$ is a member selected from the groups consisting of:
(a) phenyl optionally substituted with 1 to 3 substituents each selected from the group consisting of carboxylic acid, C(=O)—O—($C_1$-$C_4$)alkyl, halo, cyano, —C(=O)NH$_2$, ($C_1$-$C_4$)alkyl, ($C_1$-$C_4$) alkoxy, ($C_1$-$C_4$)haloalkyl, hydroxy, and hydroxy ($C_1$-$C_4$)alkyl, or
(b) ($C_1$-$C_4$)alkyl substituted with a hydroxy or a phenyl, wherein said phenyl is optionally substituted with 1 to 3 substituents each selected from the group consisting of carboxylic acid, C(=O)O($C_1$-$C_4$) alkyl, halo, cyano, —C(=O)NH$_2$, ($C_1$-$C_4$)alkyl or ($C_1$-$C_4$)alkoxy, ($C_1$-$C_4$)haloalkyl, hydroxy, and hydroxy($C_1$-$C_4$)alkyl, or, if appropriate, their pharmaceutically acceptable salts and/or isomers, tautomers, solvates, polymorphs, isotopic variations or metabolites thereof.

Still more particularly preferred are the nicotinamide derivatives of the formula (1) in which:
m and n are equal to 1,
$R_1$ is a hydrogen atom or a fluoro and $R_2$ is a hydrogen atom,
X is —O—,
$R_3$ is a phenyl optionally substituted with a substituent selected from the group consisting of halo and —C(=O)—O—($C_1$-$C_4$)alkyl,
Y is a group —C(=O)— of partial formula (1.5):
and $R_4$ is a member selected from the groups consisting of:
(a) phenyl optionally substituted with 1 to 3 substituents each selected from the group consisting of halo, ($C_1$-$C_4$)alkyl and hydroxy, or
(b) ($C_1$-$C_4$)alkyl substituted with a hydroxy or a phenyl, wherein said phenyl is optionally substituted with 1 to 3 substituents each selected from the group consisting of halo, ($C_1$-$C_4$)alkyl and hydroxy, or, if appropriate, their pharmaceutically acceptable salts and/or isomers, tautomers, solvates, polymorphs, isotopic variations or metabolites thereof.

Particularly preferred nicotinamide derivatives of the formula (1) are as described in the Examples section hereafter, i.e.

2-(4-Fluoro-phenoxy)-N-{4-[(2-hydroxy-3-methyl-benzoyl amino)-methyl]-benzyl}-nicotinamide, 3-(3-{4-[(3-Hydroxy-benzoylamino)-methyl]-benzyl carbamoyl}-pyridin-2-yloxy)-benzoic acid ethyl ester, 2-(4-fluoro-phenoxy)-N-{4-[(6-fluoro-2-hydroxy-benzoylamino)-methyl]-benzyl}-nicotinamide, 2-(4-fluoro-phenoxy)-N-{4-[(5-fluoro-2-hydroxy-benzoylamino)-methyl]-benzyl}-nicotinamide, 2-(4-fluoro-phenoxy)-N-{4-[(3-hydroxy-4-methyl-benzoylamino)-methyl]-benzyl}-nicotinamide, 2-(4-fluoro-phenoxy)-N-{4-[(3-hydroxy-benzoylamino)-methyl]-benzyl}-nicotinamide, 2-(4-fluoro-phenoxy)-N-{4-[(2-hydroxy-benzoylamino)-methyl]-benzyl}-nicotinamide, 2-(4-fluoro-phenoxy)-N-{4-[(4-hydroxy-benzoylamino)-methyl]-benzyl}-nicotinamide, 2-(4-fluoro-phenoxy)-N-{4-[(2-hydroxy-4-methyl-benzoylamino)-methyl]-benzyl}-nicotinamide,
2-(4-fluoro-phenoxy)-N-{4-[(3-hydroxy-2-methyl-benzoylamino)-methyl]-benzyl}-nicotinamide,
2-(4-fluoro-phenoxy)-N-{4-[(2-hydroxy-5-methyl-benzoylamino)-methyl]-benzyl}-nicotinamide,
5-fluoro-2-(4-fluoro-phenoxy)-N-{4-[(2-hydroxy-benzoylamino)-methyl]-benzyl}-nicotinamide,
5-fluoro-2-(4-fluoro-phenoxy)-N-{4-[(2-hydroxy-acetyl-amino)-methyl]-benzyl}-nicotinamide,
5-fluoro-2-(4-fluoro-phenoxy)-N-{4-[(4-hydroxy-benzoylamino)-methyl]-benzyl}-nicotinamide,
3-(3-{4-[(3-hydroxy-benzoylamino)-methyl]-benzylcarbamoyl}-pyridin-2-yloxy)-benzoic acid ethyl ester,
3-(3-{4-[(2-hydroxy-phenacetyl-amino)-methyl]-benzylcarbamoyl}-pyridin-2-yloxy)-benzoic acid ethyl ester,
3-(3-{4-[(3-hydroxy-phenacetyl-amino)-methyl]-benzylcarbamoyl}-pyridin-2-yloxy)-benzoic acid ethyl ester,
3-(3-{4-[(4-hydroxy-phenacetyl-amino)-methyl]-benzylcarbamoyl}-pyridin-2-yloxy)-benzoic acid ethyl ester.

The nicotinamide derivatives of formula (1) may also be optionally transformed in pharmaceutically acceptable salts. In particular, these pharmaceutically acceptable salts of the nicotinamide derivatives of the formula (1) include the acid addition and the base salts thereof.

Suitable acid addition salts are formed from mineral or organic non-toxic acids which form non-toxic salts. Suitable examples of these acid addition salts are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases, which form non-toxic salts, such as alkali metal salts, earth metal salts or addition salts with ammonia and physiologically tolerable organic amines. Suitable examples of these base salts are the sodium, potassium, aluminium, calcium, magnesium, zinc or ammonium salts as well as addition salts with triethylamine, ethanolamine, diethanolamine, trimethylamine, methylamine, propylamine, diisopropylamine, N,N-dimethylethanolamine, benzylamine, dicylohexylamine, N-benzyl-β-phenethylamine, N,N'-dibenzylethylenediamine, diphenylenediamine, quinine, choline, arginine, lysine, leucine, dibenzylamine, tris(2-hydroxyethyl)amine, or α,α,α-tris(hydroxymethyl)methylamine.

Compounds, which contain both acidic groups and basic groups can also be present in the form of internal salts or betaines, which are also included by the present invention. For a review on suitable salts see Berge et al., *J. Pharm. Sci.,* 1977, 66, p. 1–19.

Salts can generally be obtained from the nicotinamide derivatives of the formula (1) according to customary procedures known to the person skilled in the art, for example by combining with an organic or inorganic acid or base solvent or dispersant, or alternatively from other salts by anion exchange or cation exchange. The salt may precipitate from solution and be collected by filtration or may be recovered by evaporation of the solvent.

The nicotinamide derivatives of the formula (1) can also be present in stereoisomeric forms. If the nicotinamide derivatives of the formula (1) contain one or more centers of asymmetry, these can independently of one another have the (S) configuration or the (R) configuration. The invention includes all possible stereoisomers of the nicotinamide derivatives of the formula (1), for example enantiomers and diastereomers, and mixtures of two or more stereoisomeric forms, for example mixtures of enantiomers and/or diastereomers, in all ratios. The invention thus relates to enantiomers in enantiomerically pure form, both as levorotatory and dextrorotatory antipodes, in the form of racemates and in the form of mixtures of the two enantiomers in all ratios. The invention likewise relates to diastereomers in diastereomerically pure form and in the form of mixtures in all ratios. In the presence of cis/trans isomerism, the invention relates to both the cis form and the trans form and mixtures of these forms in all ratios. Individual stereoisomers can be prepared, if desired, by use of stereochemically homogeneous starting substances in the synthesis, by stereoselective synthesis or by separation of a mixture according to customary methods, for example by chromatography, crystallization or by chromatography on chiral phases. If appropriate, derivatization can be carried out before separation of stereoisomers. A stereoisomer mixture can be separated at the stage of the nicotinamide derivatives of the formula (1) or at the stage of a starting substance or of an intermediate in the course of the synthesis.

The compounds of the formula (1) according to the invention can moreover contain mobile hydrogen atoms, i.e. be present in various tautomeric forms. The present invention also relates to all tautomers of the compounds of the formula (1).

The present invention furthermore includes other types of derivatives of nicotinamide derivatives of the formula (1), for example, solvates such as hydrates and polymorphs, i.e. the various different crystalline structures of the nicotinamide derivatives according to the present invention.

The present invention also includes all suitable isotopic variations of the nicotinamide derivatives of the formula (1) or a pharmaceutically acceptable salt thereof. An isotopic variation of the nicotinamide derivatives of the formula (1) or a pharmaceutically acceptable salt thereof is defined as one in which at least one atom is replaced by an atom having the same atomic number but an atomic mass different from the atomic mass usually found in nature. Examples of isotopes that can be incorporated into the nicotinamide derivatives of the formula (1) and pharmaceutically acceptable salts thereof include isotopes of hydrogen, carbon, nitrogen, oxygen, sulphur, fluorine and chlorine such as $^2$H, $^3$H, $^{13}$C, $^{14}$C, $^{15}$N, $^{17}$O, $^{18}$O, $^{35}$S, $^{18}$F and $^{36}$Cl, respectively. Certain isotopic variations of the nicotinamide derivatives of the formula (1) and pharmaceutically acceptable salts thereof, for example, those in which a radioactive isotope such as $^3$H or $^{14}$C is incorporated, are useful in drug and/or substrate tissue distribution studies. Tritiated, i.e. $^3$H, and carbon-14, i.e. $^{14}$C, isotopes are particularly preferred for their ease of preparation and detectability. Further, substitution with isotopes such as deuterium, i.e. $^2$H, may afford certain therapeutic advantages resulting from greater metabolic stability, for example, increased in vivo half-life or reduced dosage requirements and hence may be preferred in some circumstances. Isotopic variations of the nicotinamide derivatives of the formula (1) and pharmaceutically acceptable salts thereof of this invention can generally be prepared by conventional procedures such as by the illustrative methods or by the preparations described in the Examples and Preparations sections hereafter using appropriate isotopic variations of suitable reagents.

If appropriate, the present invention also concerns the active metabolites of the nicotinamide derivatives of the formula (1), i.e. the derivatives which are formed during the cellular metabolism and that are active on organism. For example, such metabolites can be glucuronide derivatives, N-oxide derivatives or sulfonate derivatives of the compounds of the formula (1).

According to a further aspect, the present invention concerns mixtures of nicotinamide derivatives of the formula (1), as well as mixtures with or of their pharmaceutically acceptable salts, solvates, polymorphs, isomeric forms, metabolites and/or isotope forms.

According to the present invention, all the here above mentioned forms of the nicotinamide derivatives of formula (1) except the pharmaceutically acceptable salts (i.e. said solvates, polymorphs, isomeric forms, tautomers, metabolites and isotope forms), are defined as "derived forms" of the nicotinamide derivatives of formula (1) in what follows (including the claims).

The nicotinamide derivatives of formula (1), their pharmaceutically acceptable salts and/or derived forms, are valuable pharmaceutical active compounds, which are suitable for the therapy and prophylaxis of numerous disorders in which the PDE4 enzymes are involved, in particular the inflammatory disorders, allergic disorders, respiratory diseases and wounds. The nicotinamide derivatives of formula (1) and their pharmaceutically acceptable salts and derived forms as mentioned above can be administered according to the invention to animals, preferably to mammals, and in particular to humans, as pharmaceuticals for therapy or prophylaxis. They can be administered per se, in mixtures with one another or in the form of pharmaceutical preparations which permit enteral (gastric) or parenteral (non-gastric) administration and which as active constituent contain an efficacious dose of at least one nicotinamide derivative of the formula (1), its pharmaceutically acceptable salts and/or derived forms, in addition to customary pharmaceutically innocuous excipients and/or additives.

Thus, the present invention also relates to compositions containing a nicotinamide derivative of formula (1) and/or their pharmaceutically acceptable salts and/or derived forms, together with customary pharmaceutically innocuous excipients and/or additives. Such compositions are prepared according to well-known methods compatible with the standard pharmaceutical practice. Said compositions generally contain from 0.5% to 60% in weight of the active compound and from 40% to 99.5% in weight of excipients and/or additives. According to the present invention, said excipients and/or additives are agents well known to the artisan for providing favourable properties in the final pharmaceutical composition. Typical excipients and/or additives include, but are by no mean limited to, acidifying and alkalizing agents, aerosol propellants, anti-microbial agents (including anti-bacterial, anti-fungal and anti-protozoal agents), antioxidants, buffering agents, chelating agents, dermatologically active agents, dispersing agents, suspending agents, emollients, emulsifying agents, penetration enhancers, preservatives, sequestering agents, solvents, stabilizers, stiffening agents, sugars, surfactants and flavouring agents. Furthermore, said compositions are prepared in a form compatible for the intended route of administration, which is used for any given patient, as well as appropriate to the disease, disorder or condition for which any given patient is being treated. Suitable routes of administration that can be envisaged are enteral and parenteral routes of administration, such as for example the topical, oral, intranasal, pulmonary, rectal, intra-veinous, intra-arterial, intra-peritoneal, intra-thecal, intra-ventricular, intra-urethral, intra-sternal, intra-cranial, intra-muscular, subcutaneous or ocular routes.

When an administration by the oral route is intended, the nicotinamide derivatives of formula (1), their pharmaceutically acceptable salts and/or their derived forms, can be administered in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The nicotinamide derivatives of formula (1), their pharmaceutically acceptable salts and/or their derived forms, may also be administered as fast-dispersing or fast-dissolving dosage forms or in the form of a high energy dispersion or as coated particles. Suitable formulations of the nicotinamide derivatives of formula (1), their pharmaceutically acceptable salts and/or their derived forms, may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

As a general example, a formulation of the tablet could typically contain between about 0.01 mg and 500 mg of active compound whilst tablet fill weights may range from 50 mg to 1000 mg. The tablets may be manufactured by a standard process, for example by direct compression or by a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the nicotinamide derivatives of the formula (1), their pharmaceutically acceptable salts and/or their derived forms, may be combined with various sweetening or flavouring agents, colouring matter or dyes, with emulsifying and/or suspending agents and with diluents such as water, ethanol, propylene glycol and glycerin, and combinations thereof.

The nicotinamide derivatives of the formula (1), their pharmaceutically acceptable salts and/or their derived forms, can also be administered by injection, for example, intravenously, intra-arterially, intraperitoneally, intrathecally, intraventricularly, intraurethrally, intrasternally, intracranially, intramuscularly or subcutaneously, or they may be administered by infusion or needleless injection techniques. For such administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of such formulations under sterile conditions is readily accomplished by standard pharmaceutical techniques well-known to those skilled in the art.

For both oral administration and injection to human patients, the daily dosage level of the nicotinamide derivatives of the formula (1), their pharmaceutically acceptable salts and/or their derived forms, will usually be from 0.001 mg/kg to 100 mg/kg (in single or divided doses).

The nicotinamide derivatives of the formula (1), their pharmaceutically acceptable salts and/or their derived forms, can also be administered intra-nasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a nicotinamide derivative of the formula (1) and a suitable powder base such as lactose or starch.

Aerosol or dry powder formulations are preferably arranged so that each metered dose or "puff" contains from 1 $\mu$g to 4000 $\mu$g of a nicotinamide derivative of the formula (1) for delivery to the patient. The overall daily dose with an aerosol will be in the range of from 1 $\mu$g to 20 mg, which may be administered in a single dose or, more usually, in divided doses throughout the day.

The nicotinamide derivatives of the formula (1), their pharmaceutically acceptable salts and/or their derived forms, can also be administered topically, or transdermally, in the form of creams, gels, suspensions, lotions, ointments, dusting powders, sprays, foams, mousses, drug-incorporated dressings, solutions, sponges, fibres, microemulsions, films, skin patches, ointments such as petrolatum or white soft paraffin based ointments or via a skin patch or other device. Penetration enhancers may be used, and the compound may be used in combination with cyclodextrins. In addition, the compound may be delivered using iontophoresis, electropration, phonophoresis or sonophoresis. They could be administered directly onto a wound site. They could be incorporated into a coated suture. For example they can be incorporated into a lotion or cream consisting of an aqueous or oily emulsion of mineral oils, sorbitan monostearate, polysorbate 60, cetyl esters wax, cetearyl alcohol, 2-octyldodecanol, benzyl alcohol, water, polyethylene glycols and/or liquid paraffin, or they can be incorporated into a suitable ointment consisting of one or more of the following: mineral oil, liquid petrolatum, white petrolatum, propylene glycol, polyoxyethylene polyoxypropylene compound, emulsifying wax and water, or as hydrogel with cellulose or polyacrylate derivatives or other viscosity modifiers, or as a dry powder or liquid spray or aerosol with butane/propane, HFA, CFC, CO2 or other suitable propellant, optionally also including a lubricant such as sorbitan trioleate, or as a drug-incorporated dressing either as a tulle dressing, with white soft paraffin or polyethylene glycols impregnated gauze dressings or with hydrogel, hydrocolloid, alginate or film dressings.

For topical administration to human patients with acute/surgical wounds or scars, the daily dosage level of the compounds, in suspension or other formulation, could be from 0.01 to 50 mg/ml, preferably from 0.3 to 30 mg/ml. The dosage will vary with the size of the wound, whether or not the wound is open or closed or partially closed, and whether or not the skin is intact.

Alternatively, the nicotinamide derivatives of the formula (1), their pharmaceutically acceptable salts and/or their derived forms, can be rectally administered, for example in the form of a suppository of a gel, although other forms can be considered.

They may also be administered by the ocular route, in particular for ocular scarring. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

The various pharmaceutical formulations as decribed here above are also detailed in "Pharmacie galénique" from A. Lehir (Ed. Mason, 1992, $2^{nd}$ edition).

The physician in any event will determine the actual dosage which will be most suitable for any individual patient and it will vary with the age, weight, health state and sex of the patient as well as the severity of the disease, disorder or condition to treat, the optional combination with other treatment(s), the response of the particular patient and in general any factor peculiar to the concerned disease, disorder or condition and to the patient. Thus, the daily dose among men may usually contain from 50 mg to 5 g of active compound for administration singly or two or more at a time, as appropriate. There can, of course, be individual instances where higher or lower dosage ranges are merited and such are within the scope of this invention.

According to the present invention, the nicotinamide derivatives of the formula (1), their pharmaceutically acceptable salts and/or their derived forms, may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. α-, β- and γ-cyclodextrins are most commonly used and suitable examples are described in WO-A-91/11172, WO-A-94/02518 and WO-A-98/55148.

According to another embodiment of the present invention, the nicotinamide derivatives of the formula (1), or pharmaceutically acceptable salts, derived forms or compositions thereof, can also be used as a combination with one or more additional therapeutic agents to be co-administered to a patient to obtain some particularly desired therapeutic end result. The second and more additional therapeutic agents may also be a nicotinamide derivatives of the formula (1), or pharmaceutically acceptable salts, derived forms or compositions thereof, or one or more PDE4 inhibitors known in the art. More typically, the second and more therapeutic agents will be selected from a different class of therapeutic agents.

As used herein, the terms "co-administration", "co-administered" and "in combination with", referring to the nicotinamide derivatives of formula (1) and one or more other therapeutic agents, is intended to mean, and does refer to and include the following:

simultaneous administration of such combination of nicotinamide derivative(s) and therapeutic agent(s) to a patient in need of treatment, when such components are formulated together into a single dosage form which releases said components at substantially the same time to said patient, substantially simultaneous administration of such combination of nicotinamide derivative(s) and therapeutic agent(s) to a patient in need of treatment, when such components are formulated apart from each other into separate dosage forms which are taken at substantially the same time by said patient, whereupon said components are released at substantially the same time to said patient, sequential administration of such combination of nicotinamide derivative(s) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of nicotinamide derivative(s) and therapeutic agent(s) to a patient in need of treatment, when such components are formulated together into a single dosage form which releases said components in a controlled manner whereupon they are concurrently, consecutively, and/or overlappingly administered at the same and/or different times by said patient.

Suitable examples of other therapeutic agents which may be used in combination with the nicotinamide derivatives of the formula (1), or pharmaceutically acceptable salts, derived forms or compositions thereof, include, but are by no mean limited to:

(a) 5-Lipoxygenase (5-LO) inhibitors or 5-lipoxygenase activating protein (FLAP) antagonists, (b) Leukotriene antagonists (LTRAs) including antagonists of $LTB_4$, $LTC_4$, $LTD_4$, and $LTE_4$, (c) Histaminic receptor antagonists including H1 and H3 antagonists, (d) $\alpha_1$- and $\alpha_2$-adrenoceptor agonist vasoconstrictor sympathomimetic agents for decongestant use, (e) Muscarinic M3 receptor antagonists or anticholinergic agents, (f) $\beta_2$-adrenoceptor agonists, (g) Theophylline, (h) Sodium cromoglycate, (i) COX-1 inhibitors (NSAIDs) and COX-2 selective inhibitors, (j) Oral or inhaled Glucocorticosteroids, (k) Monoclonal antibodies active against endogenous inflammatory entities, (l) Anti-tumor necrosis factor (anti-TNF-$\alpha$) agents, (m) Adhesion molecule inhibitors including VLA-4 antagonists, (n) Kinin-$B_1$- and $B_2$-receptor antagonists, (o) Immunosuppressive agents, (p) Inhibitors of matrix metalloproteases (MMPs), (q) Tachykinin $NK_1$, $NK_2$ and $NK_3$ receptor antagonists, (r) Elastase inhibitors, (s) Adenosine A2a receptor agonists, (t) Inhibitors of urokinase, (u) Compounds that act on dopamine receptors, e.g. D2 agonists and (v) Modulators of the NFκ☐ pathway, e.g. IKK inhibitors, According to the present invention, combination of the nicotinamide derivatives of formula (1) with:

muscarinic M3 receptor agonists or anticholinergic agents including in particular ipratropium salts, namely bromide, tiotropium salts, namely bromide, oxitropium salts, namely bromide, perenzepine, and telenzepine, $\beta_2$-adrenoceptor agonists including albutarol, salbutamol, formoterol and salmeterol, glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, and mometasone furoate, or adenosine A2a receptor agonists, are preferred.

It is to be appreciated that all references herein to treatment include curative, palliative and prophylactic treatment. The description, which follows, concerns the therapeutic applications to which the nicotinamide derivatives of formula (1) may be put.

The nicotinamide derivatives of formula (1) inhibit the PDE4 isozyme and thereby have a wide range of therapeutic applications, as described further below, because of the essential role, which the PDE4 family of isozymes plays in the physiology of all mammals. The enzymatic role performed by the PDE4 isozymes is the intracellular hydrolysis of adenosine 3',5'-monophosphate (cAMP) within pro-inflammatory leukocytes. cAMP, in turn, is responsible for mediating the effects of numerous hormones in the body, and as a consequence, PDE4 inhibition plays a significant role in a variety of physiological processes. There is extensive literature in the art describing the effects of PDE inhibitors on various inflammatory cell responses, which in addition to cAMP increase, include inhibition of superoxide production, degranulation, chemotaxis and tumor necrosis factor (TNF) release in eosinophils, neutrophils and monocytes.

Therefore, a further aspect of the present invention relates to the nicotinamide derivatives of formula (1), or pharmaceutically acceptable salts, derived forms or compositions thereof, for use in the treatment of diseases, disorders, and conditions in which the PDE4 isozymes are involved. More specifically, the present invention also concerns the nicotinamide derivatives of formula (1), or pharmaceutically acceptable salts, derived forms or compositions thereof, for use in the treatment of diseases, disorders, and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma and wheezy infant syndrome, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated therewith, COPD that is characterized by irreversible, progressive airways obstruction, adult respiratory distress syndrome (ARDS) and exacerbation of airways hyper-reactivity consequent to other drug therapy, pneumoconiosis of whatever type, etiology, or pathogenesis, in particular pneumoconiosis that is a member selected from the group consisting of aluminosis or bauxite workers' disease, anthracosis or miners' asthma, asbestosis or steam-fitters' asthma, chalicosis or flint disease, ptilosis caused by inhaling the dust from ostrich feathers, siderosis caused by the inhalation of iron particles, silicosis or grinders' disease, byssinosis or cotton-dust asthma and talc pneumoconiosis, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis, seasonal allergic rhinitis or perennial allergic rhinitis or sinusitis of whatever type, etiology, or pathogenesis, in particular sinusitis that is a member selected from the group consisting of purulent or nonpurulent sinusitis, acute or chronic sinusitis and ethmoid, frontal, maxillary, or sphenoid sinusitis, rheumatoid arthritis of whatever type, etiology, or pathogenesis, in particular rheumatoid arthritis that is a member selected from the group consisting of acute arthritis, acute gouty arthritis, chronic inflammatory arthritis, degenerative arthritis, infectious arthritis, Lyme arthritis, proliferative arthritis, psoriatic arthritis and vertebral arthritis, gout, and fever and pain associated with inflammation, an eosinophil-related disorder of whatever type, etiology, or pathogenesis, in particular an eosinophil-related disorder that is a member selected from the group consisting of eosinophilia, pulmonary infiltration eosinophilia, Loffler's syndrome, chronic eosinophilic pneumonia, tropical pulmonary eosinophilia, bronchopneumonic aspergillosis, aspergilloma, granulomas containing eosinophils, allergic granulomatous angiitis or Churg-Strauss syndrome, polyarteritis nodosa (PAN) and systemic necrotizing vasculitis, atopic dermatitis, allergic dermatitis, contact dermatitis, or allergic or atopic eczema, urticaria of whatever type, etiology, or pathogenesis, in particular urticaria that is a member selected from the group consisting of immune-mediated urticaria, complement-mediated urticaria, urticariogenic material-induced urticaria, physical agent-induced urticaria, stress-induced urticaria, idiopathic urticaria, acute urticaria, chronic urticaria, angioedema, cholinergic urticaria, cold urticaria in the autosomal dominant form or in the acquired form, contact urticaria, giant urticaria and papular urticaria, conjunctivitis of whatever type, etiology, or pathogenesis, in particular conjunctivitis that is a member selected from the group consisting of actinic conjunctivitis, acute catarrhal conjunctivitis, acute contagious conjunctivitis, allergic conjunctivitis, atopic conjunctivitis, chronic catarrhal conjunctivitis, purulent conjunctivitis and vernal conjunctivitis, uveitis of whatever type, etiology, or pathogenesis, in particular uveitis that is a member selected from the group consisting of inflammation of all or part of the uvea, anterior uveitis, iritis, cyclitis, iridocyclitis, granulomatous uveitis, nongranulomatous uveitis, phacoantigenic uveitis, posterior uveitis, choroiditis; and chorioretinitis, psoriasis, multiple sclerosis of whatever type, etiology, or pathogenesis, in particular multiple sclerosis that is a member selected from the group consisting of primary progressive multiple sclerosis and relapsing remitting multiple sclerosis, autoimmune/inflammatory diseases of whatever type, etiology, or pathogenesis, in particular an autoimmune/inflammatory disease that is a member selected from the group consisting of autoimmune hematological disorders, hemolytic anemia, aplastic anemia, pure red cell anemia, idiopathic thrombocytopenic purpura, systemic lupus erythematosus, polychondritis, scleroderma, Wegner's granulomatosis, dermatomyositis, chronic active hepatitis, myasthenia gravis, Stevens-Johnson syndrome, idiopathic sprue, autoimmune inflammatory bowel diseases, ulcerative colitis, endocrin opthamopathy, Grave's disease, sarcoidosis, alveolitis, chronic hypersensitivity pneumonitis, primary biliary cirrhosis, juvenile diabetes or diabetes mellitus type I, keratoconjunctivitis sicca, epidemic keratoconjunctivitis, diffuse interstitial pulmonary fibrosis or interstitial lung fibrosis, idiopathic pulmonary fibrosis, cystic fibrosis, glomerulonephritis with and without nephrotic syndrome, acute glomerulonephritis, idiopathic nephrotic syndrome, minimal change nephropathy, inflammatory/hyperproliferative skin diseases, benign familial pemphigus, pemphigus erythematosus, pemphigus foliaceus, and pemphigus vulgaris, prevention of allogeneic graft rejection following organ transplantation, inflammatory bowel disease (IBD) of whatever type, etiology, or pathogenesis, in particular inflammatory bowel disease that is a member selected from the group consisting of collagenous colitis, colitis polyposa, transmural colitis, ulcerative colitis and Crohn's disease (CD), septic shock of whatever type, etiology, or pathogenesis, in particular septic shock that is a member selected from the group consisting of renal failure, acute renal failure, cachexia, malarial cachexia, hypophysial cachexia, uremic cachexia, cardiac cachexia, cachexia suprarenalis or Addison's disease, cancerous cachexia and cachexia as a consequence of infection by the human immunodeficiency virus (HIV), liver injury, pulmonary hypertension of whatever type, etiology or pathogenesis including primary pulmonary hypertension/essential hypertension, pulmonary hypertension secondary to congestive heart failure, pulmonary hypertension secondary to chronic obstructive pulmonary disease, pulmonary venous hypertension, pulmonary arterial hypertension and hypoxia-induced pulmonary hypertension, bone loss diseases, primary osteoporosis and secondary osteoporosis, central nervous system disorders of whatever type, etiology, or pathogenesis, in particular a central nervous system disorder that is a member selected from the group consisting of depression, Alzheimers disease, Parkinson's disease, learning and memory impairment, tardive dyskinesia, drug dependence, arteriosclerotic dementia and dementias that accompany Huntington's chorea, Wilson's disease, paralysis agitans, and thalamic atrophies, infection, especially infection by viruses wherein such viruses increase the production of TNF-α in their host, or wherein such viruses are sensitive to upregulation of TNF-α in their host so that their replication or other vital activities are adversely impacted, including a virus which is a member selected from the group consisting of HIV-1, HIV-2, and HIV-3, cytomegalovirus (CMV), influenza, adenoviruses and Herpes viruses including Herpes zoster and Herpes simplex, yeast and fungus infections wherein said yeast and fungi are sensitive to upregulation by TNF-α or elicit TNF-α production in their host, e.g., fungal meningitis, particularly when administered in conjunction with other drugs of choice for the treatment of systemic yeast and fungus infections, including but are not limited to, polymixins, e.g. Polymycin B, imidazoles, e.g. clotrimazole, econazole, miconazole, and ketoconazole, triazoles, e.g. fluconazole and itranazole as well as amphotericins, e.g. Amphotericin B and liposomal Amphotericin B, ischemia-reperfusion injury, ischemic heart disease, autoimmune diabetes, retinal autoimmunity, chronic lymphocytic leukemia, HIV infections, lupus erythematosus, kidney and ureter disease, urogenital and gastrointestinal disorders and prostate diseases, reduction of scar formation in the human or animal body, such as scar formation in the healing of acute wounds, and psoriasis, other dermatological and cosmetic uses, including antiphlogistic, skin-softening, skin elasticity and moisture-increasing activities.

A still further aspect of the present invention also relates to the use of the nicotinamide derivatives of formula (1), or pharmaceutically acceptable salts, derived forms or compositions thereof, for the manufacture of a drug having a PDE4 inhibitory activity. In particular, the present inventions concerns the use of the nicotinamide derivatives of formula (1), or pharmaceutically acceptable salts, derived forms or compositions thereof, for the manufacture of a drug for the treatment of inflammatory, respiratory, allergic and scar-forming diseases, disorders, and conditions and more precisely for the treatment of diseases, disorders, and conditions that are listed above.

As a consequence, the present invention provides a particularly interesting method of treatment of a mammal, including a human being, including treating said mammal with an effective amount of a nicotinamide derivative of formula (1), or a pharmaceutically acceptable salt, derived form or composition thereof. More precisely, the present invention provides a particularly interesting method of treatment of a mammal, including a human being, to treat an inflammatory, respiratory, allergic and scar-forming disease, disorder or condition, including treating said mammal with an effective amount of a nicotinamide derivative of formula (1), its pharmaceutically acceptable salts and/or derived forms.

The following examples illustrate the preparation of the nicotinamide derivatives of the formula (1):

EXAMPLE 1

2-(4-Fluoro-phenoxy)-N-{4-[(2-hydroxy-3-methyl-benzoyl amino)-methyl]-benzyl}-nicotinamide

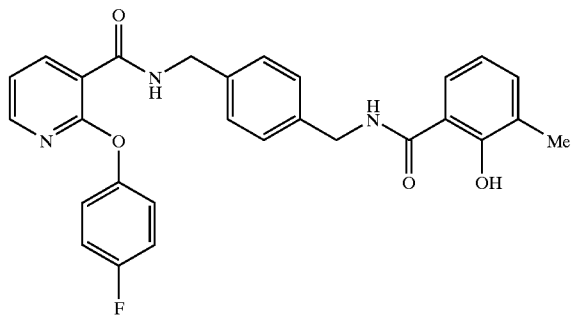

A solution of 2-Hydroxy-3-methylbenzoic acid (118 mg, 0.773 mmol), 1-hydroxybenzotriazole (157 mg, 1.16 mmol), 1-(3-dimethylaminopropyl)-3-ethylcarbodiimide hydrochloride (193 mg, 1.01 mmol), N-(4-aminomethyl-benzyl)-5-fluoro-2-(4-fluoro-phenoxy)-nicotinamide hydrochloride (300 mg, 0.773 mmol) (see Preparation 3) and N-methyl morpholine (0.17 ml, 1.55 mmol) in N,N-dimethylformamide (6 ml) was stirred under nitrogen at room temperature for 18 hours. The mixture was then partitioned between ethyl acetate (10 ml) and water (10 ml). The organic phase was separated, washed with a saturated aqueous solution of sodium chloride (10 ml) and dried over anhydrous magnesium sulphate. The solvent was then removed in vacuo and the residue was triturated with diethylether (3-fold 10 ml) giving 2-(4-fluoro-phenoxy)-N-{4-[(2-hydroxy-3-methyl-benzoylamino)-methyl]-benzyl}-nicotinamide (80 mg) as an off-white foam.

$^1$H NMR (300 MHz, DMSO-d$^6$): □=13.11 (1H, s), 8.32–8.42 (1H, m), 8.15–8.21 (1H, m), 8.08–8.14 (1H, d), 7.66–7.75 (1H, m), 7.10–7.60 (10H, m), 6.73–6.81 (1H, t), 4.37–4.56 (4H, m), 2.16 (3H, s) ppm.

LRMS (thermospray): m/z [M+H]$^+$ 486, [M+NH$_4$]$^+$503

EXAMPLES 2–15

The compounds of the following tabulated examples (Table 1) of the general formula:

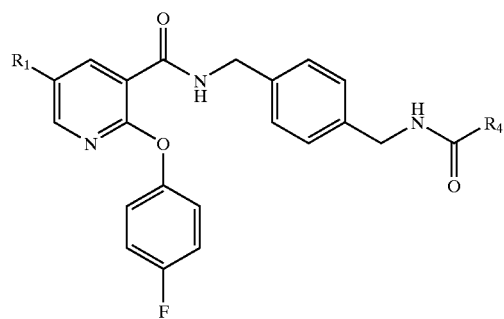

were prepared by a similar method to that of Example 1 using the appropriate amine and carboxylic acid as the starting material.

TABLE 1

| Example N° | Starting Amine Prep. N° | R₁ | R₄ |
|---|---|---|---|
| 2 | 3 | H | 3-F, 4-OH phenyl |
| 3 | 3 | H | 4-F, 3-OH phenyl (F para, OH meta) |
| 4 | 3 | H | 3-Me, 4-OH phenyl |
| 5 | 3 | H | 3-OH phenyl |
| 6 | 3 | H | 2-OH phenyl |
| 7 | 3 | H | 4-OH phenyl |
| 8 | 3 | H | 4-Me, 3-OH phenyl |
| 9 | 3 | H | 2-Me, 3-OH phenyl |
| 10 | 3 | H | 2-Me, 4-OH phenyl |
| 11[1,2] | 6 | F | 2-OH phenyl |
| 12[1] | 6 | F | -CH$_2$OH |
| 13[1,2] | 6 | F | 4-OH phenyl |

[1]The organic phase was washed sequentially with water and a saturated aqueous solution of sodium hydrogen carbonate in the work-up procedure.
[2]The compound was purified by flash column chromatography on silica gel eluting with a solvent gradient of pentane: ethyl acetate (95:5 changing to 70:30, by volume).

EXAMPLE 2

$^1$H NMR (300 MHz, DMSO-d$^6$): δ=11.28 (1H, s), 8.86–8.92 (1H, m), 8.73–8.85 (1H, m), 8.10–8.22 (2H, m), 7.16–7.36 (10H, m), 6.63–6.76 (2H, m), 4.47–4.56 (2H, d), 4.40–4.46 (2H, d) ppm.

LRMS (thermospray): m/z [M+H]$^+$ 490, [M+NH$_4$]$^+$ 507

EXAMPLE 3

$^1$H NMR (300 MHz, DMSO-d$^6$): δ=12.20 (1H, s), 9.23–9.11 (1H, m), 8.83–8.92 (1H, m), 8.17–8.21 (1H, m), 8.10–8.15 (2H, m), 7.67–7.75 (1H, m), 7.18–7.33 (10H, m), 6.86–6.96 (2H, m), 4.42–4.51 (4H, m) ppm.

LRMS (thermospray): m/z [M+H]$^+$ 490, [M+NH$_4$]$^+$ 507

EXAMPLE 4

$^1$H NMR (300 MHz, DMSO-d$^6$): δ=9.46 (1H, s), 8.83–8.92 (1H, t), 8.75–8.82 (1H, t), 8.16–8.20 (1H, d), 8.09–8.14 (1H, d), 7.15–7.32 (11H, m), 7.06–7.14 (1H, d), 4.43–4.51 (2H, d), 4.34–4.42 (2H, d), 2.13 (3H, s) ppm.

LRMS (thermospray): m/z [M+H]$^+$ 486, [M+NH$_4$]$^+$ 503

EXAMPLE 5

$^1$H NMR (300 MHz, CDCl$_3$): δ=8.54–8.61 (1H, d), 8.23–8.32 (1H, m), 8.17–8.23 (1H, m), 7.61–7.80 (1H, m), 7.35–7.40 (2H, m), 7.02–7.30 (9H, m), 6.90–7.00 (1H, m), 6.70–6.78 (1 H, m), 4.60–4.70 (2H, d), 4.48–4.59 (2H, d) ppm.

LRMS (thermospray): m/z [M+H]$^+$ 472, [M+NH$_4$]$^+$ 489.

EXAMPLE 6

$^1$H NMR (300 MHz, CDCl$_3$): δ=12.02–12.50 (1H, brs), 8.53–8.70 (1H, brs), 8.10–8.26 (2H, brs), 6.92–7.50 (12H, m), 6.63–6.88 (2H, m), 4.56–4.77 (4H, 2xm) ppm.

LRMS (thermospray): m/z [M+H]$^+$ 472, [M+NH$_4$]$^+$ 489.

EXAMPLE 7

¹H NMR (300 MHz, DMSO-d⁶): ☐=9.93 (1H, s), 8.84–8.91 (1H, t), 8.68–8.76 (1H, t), 8.17–8.21 (1H, m), 8.10–8.15 (1H, d), 7.69–7.76 (2H, d), 7.18–7.33 (9H, m), 6.74–6.81 (2H, d), 4.44–4.52 (2H, d), 4.37–4.43 (2H, d) ppm.

LRMS (thermospray): m/z [M+H]⁺ 472, [M+NH₄]⁺ 489.

EXAMPLE 8

¹H NMR (300 MHz, DMSO-d⁶): ☐=12.45–12.60 (1H, brs), 9.17–9.25 (1H, t), 8.84–8.92 (1H, t), 8.16–8.20 (1H, d), 8.09–8.14 (1H, d), 7.72–7.78 (1H, d), 7.16–7.34 (9H, m), 6.67–6.73 (2H, m), 4.40–4.58 (4H, 2xd), 2.25 (3H, s) ppm.

LRMS (thermospray): m/z [M+H]⁺ 486, [M+NH₄]⁺ 503

EXAMPLE 9

¹H NMR (300 MHz, DMSO-d⁶): ☐=9.43 (1H, s), 8.87–8.96 (1H, t), 8.60–8.67 (1H, t), 8.16–8.21 (1H, d), 8.10–8.15 (1H, d), 7.28–7.34 (1H, d), 7.20–7.28 (8H, m), 6.96–7.03 (1H, t), 6.80–6.86 (1H, d), 6.73–6.77 (1H, d), 4.47–4.54 (2H, d), 4.34–4.40 (2H, d), 2.07 (3H, s) ppm.

LRMS (thermospray): m/z [M+H]⁺ 486, [M+NH₄]⁺ 503

EXAMPLE 10

¹H NMR (300 MHz, DMSO-d⁶): ☐=12.23 (1H, s), 9.18–9.26 (1H, t), 8.82–8.92 (1H, t), 8.15–8.20 (1H, d), 8.10–8.15 (1H, d), 7.69 (1H, s), 7.12–7.34 (10H, m), 6.77–6.81 (1H, d), 4.42–4.54 (4H, 2xd), 2.20 (3H, s) ppm.

LRMS (thermospray): m/z [M+H]⁺ 486, [M+NH₄]⁺ 503

EXAMPLE 11

¹H NMR (400 MHz, DMSO-d⁶): ☐=9.24–9.31 (1H, m), 8.92–9.00 (1H, m), 8.18–8.20 (1H, d), 8.02–8.07 (1H, dd), 7.83–7.87 (1H, d), 7.35–7.40 (1H, t), 7.18–7.35 (8H, m), 6.83–6.92 (2H, t), 4.42–4.56 (4H, m) ppm.

LRMS (electrospray): m/z [M+Na]⁺ 512, [M–H]⁺ 488.

EXAMPLE 12

¹H NMR (400 MHz, DMSO-d⁶): ☐=8.93–9.00 (1H, m), 8.13–8.22 (2H, m), 8.02–8.08 (1H, m), 7.14–7.27 (8H, m), 5.38–5.43 (1H, t), 4.43–4.51 (2H, d), 4.21–4.27 (2H, d), 3.79–3.84 (2H, d) ppm.

LRMS (electrospray): m/z [M–H]⁺ 426.

EXAMPLE 13

¹H NMR (400 MHz, DMSO-d⁶): ☐=9.89 (1H, s), 8.90–8.98 (1H, t), 8.64–8.73 (1H, t), 8.19–8.21 (1H, d), 8.02–8.06 (1H, dd), 7.70–7.77 (2H, d), 7.24–7.30 (2H, d), 7.17–7.23 (6H, d), 6.73–6.79 (2H, d), 4.42–4.48 (2H, d), 4.36–4.40 (2H, d) ppm.

LRMS (electrospray): m/z [M+Na]⁺ 512, [M–H]+ 488.

EXAMPLE 14

3-(3-{4-[(3-Hydroxy-benzoylamino)-methyl]-benzyl carbamoyl}-pyridin-2-yloxy)-benzoic acid ethyl ester

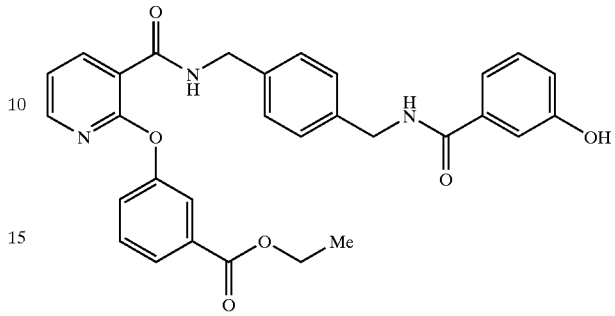

3-Hydroxy-benzoic acid (27 mg, 0.19 mmol), 1-hydroxybenzotriazole (31 mg, 0.23 mmol) and 1-(3-dimethylaminopropyl)-3-ethylcarbodiimide hydrochloride (45 mg, 0.23 mmol) were added to a solution of 3-[3-(4-aminomethyl-benzylcarbamoyl)-pyridin-2-yloxy]-benzoic acid ethyl ester hydrochloride (100 mg, 0.19 mmol) (see Preparation 9) and N-methyl morpholine (0.11 ml, 0.97 mmol) in N,N-dimethylformamide (15 ml). The reaction mixture was stirred at room temperature under a nitrogen atmosphere for 18 hours, concentrated in vacuo and the residue partitioned between dichloromethane (20 ml) and water (20 ml). The organic phase was separated, washed with a saturated aqueous solution of sodium chloride (20 ml), dried over anhydrous magnesium sulphate and concentrated under reduced pressure. The residue was then purified by flash column chromatography on silica gel eluting with a solvent gradient of dichloromethane:methanol (99:1 changing to 98:1, by volume) giving 3-(3-{4-[(3-hydroxy-benzoylamino)-methyl]-benzylcarbamoyl}-pyridin-2-yloxy)-benzoic acid ethyl ester (45 mg) as an off-white foam.

¹H NMR (400 MHz, CDCl₃): ☐=8.54–8.60 (1H, d), 8.21–8.38 (2H, t+brs), 8.17–8.20 (1H, d), 7.86–7.92 (1H, d), 7.78 (1H, s), 7.41–7.48 (1H, t), 7.28–7.37 (2H, m), 7.08–7.26 (6H, m), 6.86–6.95 (2H, m) 4.61–4.67 (2H, d), 4.45–4.53 (2H, d), 4.30–4.37 (2H, quart), 1.31–1.38 (3H, t) ppm.

LRMS (electrospray): m/z [M+H]⁺ 526, [M+Na]⁺ 548, [M–H]⁺ 524.

EXAMPLES 15–18

The compounds of the following tabulated examples (Table 2) of the general formula:

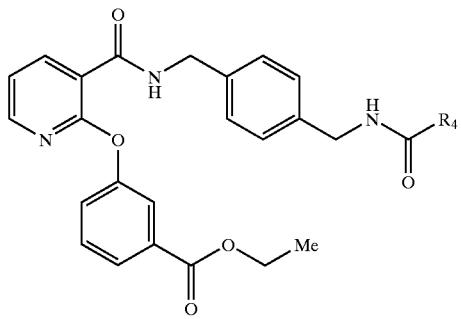

were prepared by a similar method to that of Example 14 using the appropriate carboxylic acid starting material.

TABLE 2

| Example N° | Starting Amine Prep. N° | R4 |
|---|---|---|
| 15 | 9 | |
| 16 | 9 | |
| 17 | 9 | |
| 18 | 9 | |

EXAMPLE 15

$^1$H NMR (400 MHz, CDCl$_3$): □=8.90–9.10 (1H, brs), 8.49–8.53 (1H, d), 8.28–8.34 (1H, m), 8.13–8.16 (1H, d), 7.87–7.92 (1H, d), 7.77 (1H, s), 7.53–7.59 (2H, d), 7.40–7.47 (1H, t), 7.28–7.33 (1H, m), 7.14–7.26 (5H, m, partially masked by solvent), 7.08–7.13 (1H, t), 6.75–6.81 (1H, t), 6.66–6.73 (2H, d), 4.58–4.66 (2H, d), 4.46–4.52 (2H, d), 4.28–4.34 (2H, quartet), 1.31–1.38 (3H, t) ppm.

LRMS (electrospray): m/z [M+H]$^+$ 526, [M+Na]$^+$ 548, [M–H]$^+$ 524.

EXAMPLE 16

$^1$H NMR (400 MHz, CDCl$_3$): □=9.61 (1H, s), 8.54–8.60 (1H, d), 8.14–8.21 (2H, m), 7.91–7.96 (1H, d), 7.72–7.74 (1H, m), 7.43–7.49 (1H, t), 7.29–7.33 (1H, d), 7.19–7.24 (2H, m), 7.08–7.18 (4H, m), 6.90–7.00 (2H, m), 6.73–6.80 (2H, m), 4.58–4.63 (2H, d), 4.29–4.39 (4H, m), 3.56 (2H, s), 1.35–1.41 (3H, t) ppm.

LRMS (electrospray): m/z [M+H]$^+$ 540, [M+Na]$^+$ 562, [M–H]$^+$ 538.

EXAMPLE 17

$^1$H NMR (400 MHz, CDCl$_3$): □=8.52–8.59 (1H, d), 8.19–8.25 (1H, m), 8.16–8.19 (1H, d), 7.90–7.94 (1H, d), 7.78 (1H, s), 7.44–7.49 (1H, t), 7.28–7.32 (1H, d), 7.18–7.23 (2H, d), 7.04–7.18 (4H, m), 6.64–6.73 (3H, m), 6.28–6.35 (1H, m), 4.58–4.66 (2H, d), 4.26–4.38 (4H, m), 3.42 (2H, s), 1.33–1.38 (3H, t) ppm.

LRMS (electrospray): m/z [M–H]$^+$ 538.

EXAMPLE 18

$^1$H NMR (400 MHz, CDCl$_3$): □=8.55–8.61 (1H, d), 8.18–8.23 (1H, m), 8.15–8.18 (1H, d), 7.90–7.94 (1H, d), 7.78 (1H, s), 7.43–7.49 (1H, t), 7.26–7.30 (1H, d), 7.18–7.25 (2H, m), 7.04–7.17 (3H, m), 6.95–7.01 (2H, d), 6.64–6.75 (3H, m), 6.17–6.24 (1H, m), 4.58–4.68 (2H, d), 4.30–4.40 (4H, m), 3.46 (2H, s), 1.32–1.40 (3H, t) ppm.

LRMS (electrospray): m/z [M+H]$^+$ 540, [M+Na]$^+$ 562, [M–H]$^+$ 538.

The following Preparations describe the preparation of certain intermediates used in the preceding Examples.

PREPARATION 1

(4-Aminomethyl-benzyl)-carbamic acid tert-butyl ester

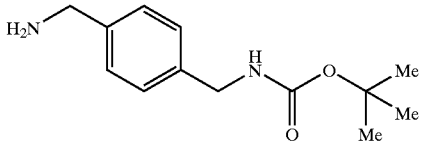

A solution of di-tert-butyl-dicarboxylate (4.62 g, 21.2 mmol) dissolved in dichloromethane (50 ml) was added to a solution of 4-aminomethyl-benzylamine (14.4 g, 106 mmol) in dichloromethane (50 ml) at 0° C. under an atmosphere of nitrogen. The reaction mixture was allowed to warm to room temperature and stirred for 18 hours. The reaction mixture was then washed sequentially with water (100 ml) and a 10% aqueous solution of citric acid (200 ml) and the organic phase disgarded. The pH of the aqueous phase was then adjusted to pH higher than 8 by addition of 0.88 ammonia and extracted with dichloromethane (3-fold 200 ml). The combined organic extracts were then dried over anhydrous magnesium sulphate and the solvent removed in vacuo giving (4-aminomethyl-benzyl)-carbamic acid tert-butyl ester (4.29 g) as a white solid.

$^1$H NMR (400 MHz, CDCl$_3$): δ=7.22–7.26 (4H, d), 4.80–4.90 (1H, brs), 4.23–4.30 (2H, m), 3.82 (2H, s), 1.43 (2H, s), 1.38 (2H, s) ppm.

LRMS (electrospray): m/z [M–H]$^+$ 237.

PREPARATION 2

[4-({[2-(4-Fluoro-phenoxy)-pyridine-3-carbonyl]-amino}-methyl)-benzyl]-carbamic acid tert-butyl ester

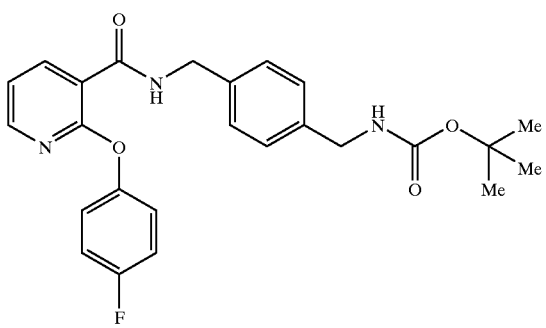

2-(4-Fluoro-phenoxy)-nicotinic acid (see reference Patent application WO 98/45268) (6.20 g, 26 mmol), 1-hydroxybenzotriazole (5.39 g, 40 mmol) and 1-(3-dimethylaminopropyl)-3-ethylcarbodiimide hydrochloride (6.62 g, 34 mmol) were disolved in N,N-dimethylformamide (50 ml) at room temperature and (4-aminomethyl-benzyl)-carbamic acid tert-butyl ester (6.28 g, 26 mmol) (see Preparation 1) added followed by addition of N-methyl morpholine (4.4 ml, 40 mmol). The reaction mixture was stirred under an atmosphere of nitrogen at room temperature for 18 hours, and then partitioned between ethyl acetate (100 ml) and water (100 ml) and the organic layer separated. The organic phase was then washed with a saturated aqueous solution of sodium chloride (100 ml), dried over anhydrous magnesium sulphate and the solvent removed in vacuo. The residue was triturated with diethylether (15 ml) giving [4-({[2-(4-fluoro-phenoxy)-pyridine-3-carbonyl]-amino}-methyl)-benzyl]-carbamic acid tert-butyl ester (9.52 g) as an off-white solid.

$^1$H NMR (300 MHz, CDCl$_3$): δ=8.56–8.76 (1H, m), 8.06–8.14 (2H, m), 6.96–7.40 (9H, m, partialy masked by solvent), 4.58–4.95 (3H, m), 4.20–4.40 (2H, brs), 1.56 (9H, s) ppm.

LRMS (thermospray): m/z [M+NH$_4$]$^+$ 469.

PREPARATION 3

N-(4-Aminomethyl-benzyl)-2-(4-fluoro-phenoxy)-nicotinamide hydrochloride

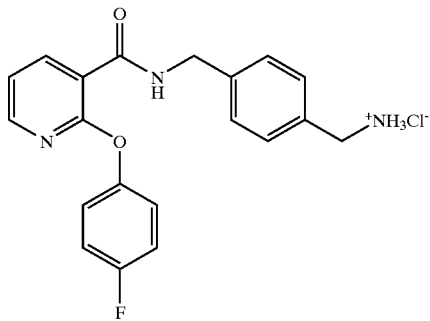

[4-({[2-(4-Fluoro-phenoxy)-pyridine-3-carbonyl]-amino}-methyl)-benzyl]-carbamic acid tert-butyl ester (9.51 g, 21 mmol) (see Preparation 2) was dissolved in dichloromethane (60 ml) and hydrogen chloride gas bubbled into the solution at 0° C. until the solution became saturated (30 minutes). The reaction mixture was then stirred under an atmosphere of nitrogen at room temperature for a further 1 hour before removal of the solvent in vacuo. The resultant white precipitate was triturated with diethylether (3-fold 10 ml) giving N-(4-aminomethyl-benzyl)-5-fluoro-2-(4-fluoro-phenoxy)-nicotinamide hydrochloride (7.92 g) as a white solid.

$^1$H NMR (300 MHz, DMSO-d$^6$): δ=8.96–9.07 (1H, m), 8.40–8.60 (2H, m), 8.17–8.22 (1H, d), 8.11–8.16 (1H, m), 7.36–7.44 (4H, m), 7.18–7.33 (5H, m), 4.43–4.58 (2H, m, partially masked by solvent), 3.86–3.99 (2H, m) ppm.

LRMS (thermospray): m/z [M+H]$^+$ 352.

PREPARATION 4

(4-{[2-Chloro-5-fluoro-pyridine-3-carbonyl)-amino]-methyl}-benzyl)-carbamic acid tert-butyl ester

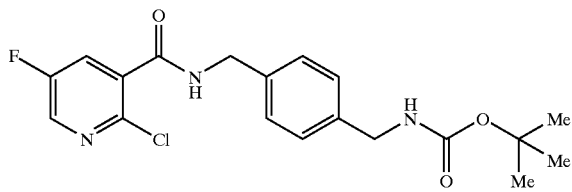

2-Chloro-5-fluoro-nicotinic acid (see Preparation 10) (2.0 g, 11.4 mmol), 1-hydroxybenzotriazole (1.85 g, 13.7 mmol) and 1-(3-dimethylaminopropyl)-3-ethylcarbodiimide hydrochloride (2.62 g, 13.7 mmol) were stirred in N,N-dimethylformamide (50 ml) at room temperature and (4-aminomethyl-benzyl)-carbamic acid tert-butyl ester (2.69 g, 11.4 mmol) (see Preparation 1) added followed by addition of N-methyl morpholine (2.5 ml, 22.8 mmol). The reaction mixture was then stirred under an atmosphere of nitrogen at room temperature for 18 hours, partitioned between dichloromethane (100 ml) and water (100 ml), and the organic layer separated. The organic layer was then washed with a saturated aqueous solution of sodium chloride (100 ml), dried over anhydrous magnesium sulphate and the solvent removed in vacuo to give (4-{[2-chloro-5-fluoro-pyridine-3-carbonyl)-amino]-methyl)-benzyl)-carbamic acid tert-butyl ester (4.08 g) as a white solid.

$^1$H NMR (400 MHz, DMSO-d$^6$): δ=9.10–9.17 (1H, t), 8.52–8.54 (1H, d), 7.99–8.04 (1H, dd), 7.26–7.35 (3H, m), 7.18–7.22 (2H, d), 4.39–4.44 (2H, d), 4.06–4.11 (2H, d), 1.38 (9H, s) ppm.

LRMS (electrospray): m/z [M+Na]$^+$ 416, [M−H]$^+$ 392.

PREPARATION 5

[4-({[5-Fluoro-2-(4-fluoro-phenoxy)-pyridine-3-carbonyl]-amino}-methyl)-benzyl]-carbamic acid tert-butyl ester

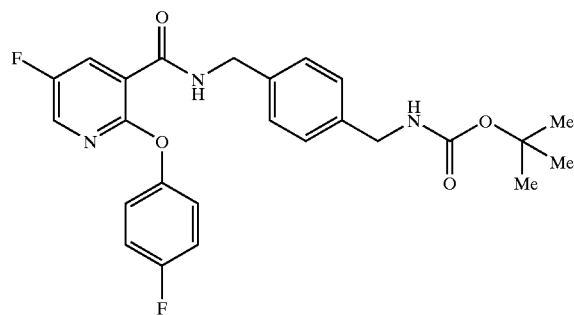

(4-{[2-Chloro-5-fluoro-pyridine-3-carbonyl)-amino]-methyl)-benzyl)-carbamic acid tert-butyl ester (100 mg, 0.29 mmol) (see Preparation 4), 4-fluorophenol (28 mg, 0.29 mmol) and caesium carbonate (800 mg, 2.5 mmol) were stirred in N,N-dimethylformamide (10 ml) at 60° C. under an atmosphere of nitrogen for 18 hours. The reaction mixture was then partitioned between ethyl acetate (20 ml) and water (20 ml), and the organic layer separated. The organic layer was then washed with a saturated aqueous solution of sodium chloride (3-fold 10 ml), the solvent removed in vacuo and the residue purified by flash column chromatography on silica gel eluting with a solvent gradient of 5:95 changing to 30:70, by volume, ethyl acetate:pentane to give [4-({[5-fluoro-2-(4-fluoro-phenoxy)-pyridine-3-carbonyl]-amino}-methyl)-benzyl]-carbamic acid tert-butyl ester (57 mg) as a white foam.

$^1$H NMR (400 MHz, DMSO-d$^6$): δ=8.97–9.02 (1H, t), 8.19–8.21 (1H, d), 8.03–8.08 (1H, dd), 7.30–7.36 (1H, m), 7.19–7.30 (6H, m), 7.11–7.16 (2H, d), 4.44–4.50 (2H, d), 4.03–4.08 (2H, d), 1.36 (9H, s) ppm.

LRMS (electrospray): m/z [M+Na]$^+$ 492, [M−H]$^+$ 468.

PREPARATION 6

N-(4-Aminomethyl-benzyl)-5-fluoro-2-(4-fluoro-phenoxy)-nicotinamide hydrochloride

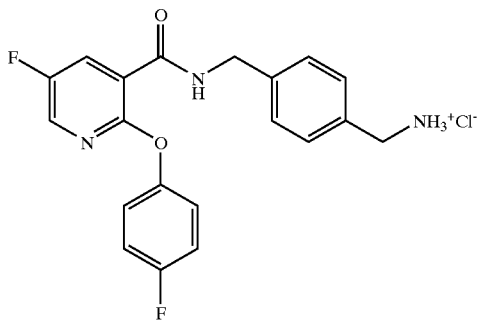

[4-({[5-Fluoro-2-(4-fluoro-phenoxy)-pyridine-3-carbonyl]-amino}-methyl)-benzyl]-carbamic acid tert-butyl ester (1.62 g, 3.44 mmol) (see Preparation 5) was dissolved in a 2.25 M solution of hydrochloric acid in methanol (100 ml) and the mixture stirred at room temperature under an atmosphere of nitrogen for 4 hours before removing the solvent in vacuo. The residue was dissolved in water (50 ml), the pH adjusted to pH higher than 8 by addition of sodium hydrogen carbonate and extracted with dichloromethane (3-fold 50 ml). The combined organic extracts were dried over anhydrous magnesium sulphate and concentrated in vacuo to give N-(4-aminomethyl-benzyl)-5-fluoro-2-(4-fluoro-phenoxy)-nicotinamide hydrochloride (1.25 mg) as a gum.

PREPARATION 7

(4-{[(2-Chloro-pyridine-3-carbonyl)-amino]-methyl}-benzyl)-carbamic acid tert-butyl ester

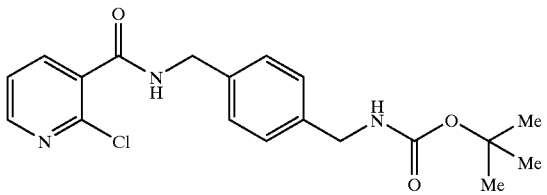

2-Chloro-nicotinic acid (2.86 g, 18.2 mmol), 1-hydroxybenzotriazole (3.0 g, 21.8 mmol) and 1-(3-dimethylaminopropyl)-3-ethylcarbodiimide hydrochloride (4.18 g, 21.8 mmol) were dissolved in N,N-dimethylformamide (50 ml) at room temperature and (4-aminomethyl-benzyl)-carbamic acid tert-butyl ester (4.29 g, 18.2 mmol) (see Preparation 1) added followed by addition of N-methyl morpholine (4 ml, 36.3 mmol). The reaction mixture was stirred under an atmosphere of nitrogen at room temperature for 18 hours, then partitioned between ethyl acetate (100 ml) and water (100 ml) and the organic layer separated. The organic layer was then washed with a saturated aqueous solution of sodium chloride (100 ml), dried over anhydrous magnesium sulphate and the solvent removed in vacuo. The residue was then triturated with diethylether (2-fold 10 ml) to give (4-{[(2-chloro-pyridine-3-carbonyl)-amino]-methyl}-benzyl)-carbamic acid tert-butyl ester (6.71 g) as a white solid.

$^1$H NMR (400 MHz, DMSO-d$^6$): δ=9.01–9.08 (1H, t), 8.43–8.47 (1H, m), 7.89–7.93 (1H, d), 7.45–7.50 (1H, m), 7.30–7.37 (1H, m), 7.26–7.31 (2H, d), 7.17–7.21 (2H, d), 4.39–4.43 (2H, d), 4.03–4.10 (2H, d), 1.37 (9H, s) ppm.

LRMS (electrospray): m/z [M–H]$^+$ 374.

PREPARATION 8

3-{3-[4-tert-Butoxycarbonylamino-methyl)-benzylcarba-moyl]-pyridin-2-yloxy}-benzoic acid ethyl ester

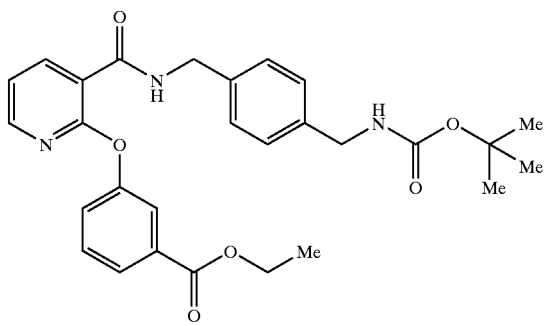

(4-{[(2-Chloro-pyridine-3-carbonyl)-amino]-methyl}-benzyl)-carbamic acid tert-butyl ester (12.0 g, 32.2 mmol) (see Preparation 7), 3-hydroxy-benzoic acid ethyl ester (6.42 g, 38.6 mmol) and caesium carbonate (15.7 g, 48.3 mmol) were stirred in dioxan (180 ml) at 70° C. under an atmosphere of nitrogen for 18 hours. Starting material remained, so a further aliquot of 3-hydroxy-benzoic acid ethyl ester (6.42 g, 38.6 mmol) and caesium carbonate (15.7 g, 48.3 mmol) were added along with dioxan (420 ml) and N,N-dimethylformamide (40 ml) and the reaction stirred at 70° C. for a further 22 hours. The solvent was then removed under reduced pressure, the residue partitioned between ethyl acetate (200 ml) and water (200 ml), and the organic layer separated. The organic layer was then washed with a saturated aqueous solution of sodium chloride (3-fold 100 ml), the solvent removed in vacuo and the residue purified by flash column chromatography on silica gel eluting with a solvent gradient of 0:100 changing to 50:50, by volume, ethyl acetate:hexane to give 3-{3-[4-tert-butoxycarbonylamino-methyl)-benzylcarbamoyl]-pyridin-2-yloxy}-benzoic acid ethyl ester (7.42 mg) as an off-white foam.

$^1$H NMR (400 MHz, DMSO-d$^6$): δ=8.92–8.98 (1H, t), 8.18–8.21 (1H, d), 8.14–8.18 (1H, d), 7.81–7.85 (1H, d), 7.77 (1H, s), 7.54–7.60 (1H, t), 7.46–7.50 (1H, m), 7.27–7.31 (2H, d), 7.22–7.26 (1H, m), 7.14–7.18 (3H, d), 4.47–4.51 (2H, d), 4.29–4.35 (2H, quart), 4.04–4.08 (2H, d), 1.37 (9H, s), 1.28–1.35 (3H, t) ppm.

LRMS (electrospray): m/z [M+Na]$^+$ 528, [M–H]$^+$ 504.

PREPARATION 9

[N-(4-Aminomethyl-benzyl)-2-(4-fluoro-phenoxy)]-nicotinamide hydrochloride

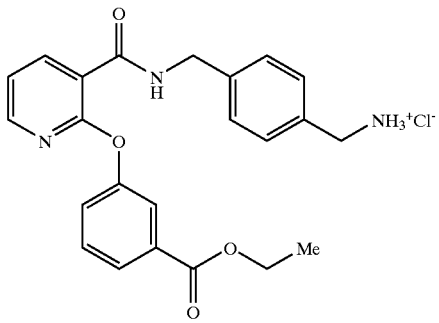

3-{3-[4-tert-Butoxycarbonylamino-methyl)-benzylcarbamoyl]-pyridin-2-yloxy}-benzoic acid ethyl ester (7.42 g, 14.7 mmol) (see Preparation 8) was dissolved in dichloromethane (100 ml) and hydrogen chloride gas bubbled through the solution at 0° C. until the solution became saturated (30 minutes). The solvent was removed in vacuo giving [N-(4-aminomethyl-benzyl)-2-(4-fluoro-phenoxy)]-nicotinamide hydrochloride (7.16 mg) as a white solid.

$^1$H NMR (400 MHz, DMSO-d$^6$): δ=9.48–9.54 (1H, m), 8.83–9.03 (3H, brs), 8.62–8.66 (1H, m), 8.57–8.63 (1H, d), 8.35–8.42 (1H, d), 8.22 (1H, s), 8.01–8.08 (1H, t), 7.93–7.98 (1H, d), 7.81–7.91 (4H, m), 7.68–7.74 (1H, d), 4.94–5.01 (2H, d), 4.76–4.81 (2H, quart), 4.36–4.42 (2H, m), 1.75–1.80 (3H, t) ppm.

LRMS (electrospray): m/z [M+H]$^+$ 406.

PREPARATION 10

2-Chloro-5-fluoro nicotinic acid

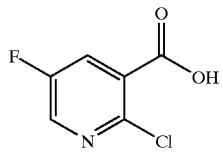

Ethyl-2-chloro-5-fluoro-nicotinoate (50.4 g, 0.247 mol) (see reference J. Med. Chem., 1993, 36(18), 2676–88) was dissolved in tetrahydrofuran (350 ml) and a 2 M aqueous solution of lithium hydroxide (247 ml, 0.495 mol) added. The reaction mixture was stirred at room temperature for 3 days. The pH of the solution was reduced to pH equal to 1 by addition of 6N hydrochloric acid and then extracted with dichloromethane. The combined extracts were dried over anhydrous magnesium sulphate and the solvent removed in vacuo to give a solid which was triturated with diethyl ether and then dried in vacuo to give 2-chloro-5-fluoro nicotinic acid (40.56 g) as a white solid.

$^1$H NMR (400 MHz, DMSO-d$^6$): δ=8.20 (1H, s), 8.62 (1H, s) ppm.

LRMS (electrospray): m/z [M+H]$^+$ 174.

In vitro Activity of the Nicotinamide Derivatives

The PDE4 inhibitory activity of the nicotinamide derivatives of the formula (1) is determined by the ability of compounds to inhibit the hydrolysis of cAMP to AMP by PDE4 (see also reference 1). Tritium labelled cAMP is incubated with PDE4. Following incubation, the radiolabelled AMP produced is able to bind ytrium silicate SPA beads. These SPA beads subsequently produce light that can be quantified by scintillation counting. The addition of a PDE4 inhibitor prevents the formation of AMP from cAMP and counts are diminished. The IC$_{50}$ of a PDE4 inhibitor can be defined as the concentration of a compound that leads to a 50% reduction in counts compared to the PDE4 only (no inhibitor) control wells.

The anti-inflammatory properties of the nicotinamide derivatives of the formula (1) are demonstrated by their ability to inhibit TNFα release from human peripheral blood mononuclear cells (see also reference 2). Venous blood is collected from healthy volunteers and the mononuclear cells purified by centrifugation through Histopaque (Ficoll) cushions. TNFα production from these cells is stimulated by addition of lipopolysaccharide. After 18 hours incubation in the presence of LPS, the cell supernatant is removed and the concentration of TNFα in the supernatant determined by ELISA. Addition of PDE4 inhibitors reduces the amount of TNFα produced. An IC$_{50}$ is determined which is equal to the concentration of compound that gives 50% inhibition of TNFα production as compared to the LPS stimulated control wells.

All the examples were tested in the assay described above and found to have an IC$_{50}$ (TNFα screen) of less than 500 nM. And for most of the tested compounds, they were found to have an IC$_{50}$ (TNFα screen) of even less than 200 nM.

References

1. Thompson J W, Teraski W L, Epstein P M, Strada S J., "Assay of nucleotidephosphodiesterase and resolution of multiple molecular forms of the isoenzyme", *Advances in cyclic nucleotides research,* edited by Brooker G, Greengard P, Robinson G A. Raven Press, New York 1979, 10, p. 69–92.
2. Yoshimura T, Kurita C, Nagao T, Usami E, Nakao T, Watanabe S, Kobayashi J, Yamazaki F, Tanaka H, Nagai H., "Effects of cAMP-phosphodiesterase isozyme inhibitor on cytokine production by lipopolysaccharide-stimulated human peripheral blood mononuclear cells", *Gen. Pharmacol.,* 1997, 29(4), p. 63

What is claimed is:

1. A compound of the formula (1):

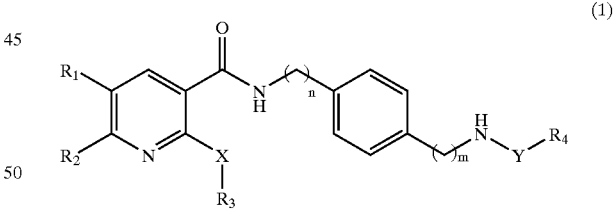

(1)

wherein;
   m is 0, 1, 2 or 3;
   n is 0, 1, 2 or 3;
   $R_1$ and $R_2$ are each independently hydrogen, halo, cyano, $(C_1-C_4)$alkyl or $(C_1-C_4)$alkoxy;
   X is —O—, —S— or —NH—;
   $R_3$ is:
     (a) phenyl, naphthyl, heteroaryl or $(C_3-C_8)$cycloalkyl, each optionally substituted independently with 1 to 3 halo, cyano, $(C_1-C_4)$alkyl, $(C_1-C_4)$alkoxy, $(C_1-C_4)$thioalkyl, —C(=O)NH$_2$, —C(=O)NH(($C_1-C_4$) alkyl), hydroxy, —O—C(=O)($C_1-C_4$)alkyl, —C(=O)—O—($C_1-C_4$)alkyl or hydroxy($C_1-C_4$) alkyl; or (b) a bicyclic group of the following formula:

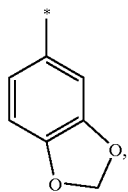 (1.1)

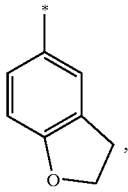 (1.2)

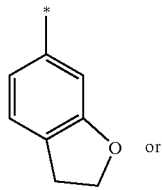 or (1.3)

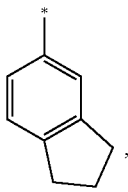 (1.4)

where the symbol "*" in the definition of $R_3$ indicates the point of attachment of each partial formula (1.1) through (1.4) to the remaining portion of formula (1);

Y is

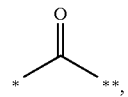 (1.5)

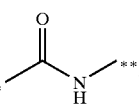 (1.6)

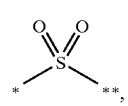 (1.7)

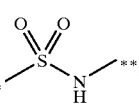 (1.8)

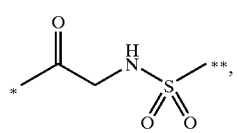 (1.9)

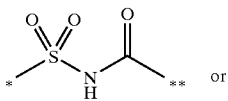 or (1.10)

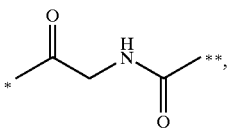 (1.11)

where the symbol "*" in the definition of Y indicates the point of attachment of each partial formula (1.5) through (1.11) to the remaining portions —NH— of formula (I) and "**" in the definition of V indicates the point of attachment of each partial formula (1.5) through (1.11) to the remaining portions —$R_4$ of formula (1); and $R_4$ is:

(a) phenyl, naphthyl or heteroaryl, each optionally substituted independently with 1 to 3 carboxy, —C(=O)—O—($C_1$-$C_4$)alkyl, halo, cyano, —C(=O)NH$_2$, ($C_1$-$C_4$)alkyl, ($C_1$-$C_4$)alkoxy ($C_1$-$C_4$)haloalkyl, hydroxy or hydroxy($C_1$-$C_4$)alkyl; or (b) ($C_1$-$C_4$)alkyl optionally substituted with hydroxy, carboxyl, C(=O)—O—($C_1$-$C_4$)alkyl, phenyl, naphthyl or heteroaryl wherein said phenyl, naphthyl and heteroaryl are each optionally substituted independently with 1 to 3 carboxy, —C(=O)O($C_1$-$C_4$)alkyl, halo, cyano, —C(=O)NH$_2$, ($C_1$-$C_4$)alkyl, ($C_1$-$C_4$)alkoxy, ($C_1$-$C_4$)haloalkyl, hydroxy or hydroxy($C_1$-$C_4$)alkyl;

provided that the compounds wherein 1) m is different from 0 simultaneously with Y representing the partial formula (1.5) and $R_4$ representing a non-substituted ($C_1$-$C_4$)alkyl are excluded;

2) m is equal to 0 simultaneously with Y representing the partial formula (1.5) and $R_4$ representing a phenyl, a naphthyl or a heteroaryl each optionally substituted with 1 to 3 substituents independently selected from the proud consisting of carboxylic acid, halo, cyano, ($C_1$-$C_4$)alkyl, ($C_1$-$C_4$)alkoxy, ($C_1$-$C_4$)haloalkyl, hydroxy and hydroxy($C_1$-$C_4$) alkyl or $R_4$ representing a ($C_1$-$C_4$)alkyl optionally substituted with a hydroxy, carboxylic acid, or a heteroaryl, which is optionally substituted with 1 to 3 substituents independently selected from the group consisting of carboxylic acid, halo, cyano, ($C_1$-$C_4$) alkyl, ($C_1$-$C_4$)alkoxy, hydroxy and hydroxy($C_1$-$C_4$) alkyl are excluded; and 3) m is eaual to 0 sImultaneously with Y representing the partial formula (1.6) and $R_4$ representing a phenyl or a naphtyl, each optionally substituted with 1 to 3 substituents independently selected from the group consisting of carboxylic acid, halo, cyano, ($C_1$-$C_4$) alkyl, ($C_1$-$C_4$)alkoxy, ($C_1$-$C_4$)haloalkyl, hydroxy and hydroxy($C_1$-$C_4$)alkyl are excluded;

and provided that 2-(4-fluoro-phenoxy)-N-(4-methanesulfoxyamino-benzyl)-nicotinamide is excluded;

or a pharmaceutically acceptable salt, thereof.

2. A compound of claim 1 wherein:

m and n are each 1;

$R_1$ and $R_2$ are each independently hydrogen, halo, cyano, $(C_1-C_4)$alkyl or $(C_1-C_4)$alkoxy;

X is —O—;

$R_3$ is:

(a) phenyl, naphthyl, heteroaryl or $(C_3-C_8)$cycloalkyl, each optionally substituted independently with 1 to 3 halo, cyano, $(C_1-C_4)$alkyl, $(C_1-C_4)$alkoxy, $(C_1-C_4)$thioalkyl, —C(=O)NH$_2$, —C(=O)NH(($C_1-C_4$) alkyl, hydroxy, —O—C(=O)($C_1-C_4$)alkyl, —C(=O)—O—($C_1-C_4$)alkyl or hydroxy($C_1-C_4$)alkyl; or (b) a bicyclic group of the formula:

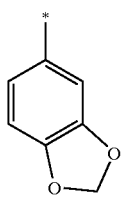

(1.1)

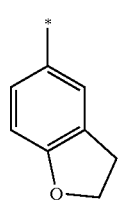

(1.2)

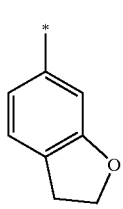

(1.3)

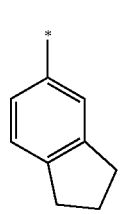

(1.4)

where the symbol "*" in the definition of $R_3$ indicates the point of attachment of each partial formula (1.1) through (1.4) to the remaining portion of formula (1);

Y is —C(=O)—; and $R_4$ is:

(a) phenyl, naphthyl or heteroaryl, each optionally substituted independently with 1 to 3 carboxy, —C(=O)—O—($C_1-C_4$)alkyl, halo, cyano, —C(=O)NH$_2$, ($C_1-C_4$)alkyl, ($C_1-C_4$)alkoxy, ($C_1-C_4$)haloalkyl, hydroxy and hydroxy($C_1-C_4$)alkyl or (b) ($C_1-C_4$alkyl substituted with a hydroxy, carboxylic acid, C(=O)—O—($C_1-C_4$)alkyl, phenyl, naphthyl or heteroaryl group wherein said pheny), naphthyl and heteroaryl are each optionally substituted with 1 to 3 substituents each selected from the group consisting of carboxylic acid, C(=O)O($C_1-C_4$)alkyl, halo, cyano, —C(=O)NH$_2$, ($C_1-C_4$)alkyl, ($C_1-C_4$)alkoxy, ($C_1-C_4$) haloalkyl, hydroxy, and hydroxy($C_1-C_4$)alkyl, or a pharmaceutically acceptable salt thereof.

3. A compound according to claim 1 wherein:

m and n are each 1;

$R_1$ and $R_2$ are each independently hydrogen, halo and methyl;

X is —O—;

$R_3$ is a phenyl optionally substituted independently with 1 to 3 halo, cyano, ($C_1-C_4$)alkyl, ($C_1-C_4$)alkoxy, ($C_1-C_4$)thioalkyl, —C(=O)NH$_2$, —C(=O)NH (($C_1-C_4$)alkyl), hydroxy, —O—C(=O)($C_1-C_4$)alkyl, —C(=O)—O—($C_1-C_4$)alkyl or hydroxy($C_1-C_4$) alkyl;

Y is —C(=O)—; and $R_4$ is:

(a) phenyl optionally substituted independently with 1 to 3 carboxy, —C(=O)—O—($C_1-C_4$)alkyl, halo, cyano, —C(=O)NH$_2$, ($C_1-C_4$)alkyl, ($C_1-C_4$)alkoxy, ($C_1-C_4$) haloalkyl, hydroxy or hydroxy($C_1-C_4$)alkyl; or (b) ($C_1-C_4$)alkyl substituted with hydroxy or phenyl, wherein said phenyl is optionally substituted independently with 1 to 3 carboxy, —C(=O)O($C_1-C_4$)alkyl, halo, cyano, —C(=O)NH$_2$, ($C_1-C_4$)alkyl or ($C_1-C_4$) alkoxy, ($C_1-C_4$)haloalkyl, hydroxy or hydroxy($C_1-C_4$) alkyl;

or a pharmaceutically acceptable salt thereof.

4. A compound according to claim 1 wherein:

m and n are each 1;

$R_1$ is hydrogen or fluoro and $R_2$ is hydrogen;

X is —O—;

$R_3$ is phenyl optionally substituted with halo or —C(=O)—O—($C_1-C_4$)alkyl;

Y is —C(=O)—; and $R_4$ s:

(a) phenyl optionally substituted independently with 1 to 3 halo, ($C_1-C_4$)alkyl or hydroxy; or (b) ($C_1-C_1$)alkyl substituted with hydroxy or phenyl, wherein said phenyl is optionally substituted independently with 1 to 3 halo, ($C_1-C_4$)alkyl and hydroxy;

or a pharmaceutically acceptable salt thereof.

5. A compound according to claim 1 which is:

2-(4-fluro-phenoxy)-N-{4-[(2-hydroxy-3-methyl-benzoyl amino)-methyl]-benzyl}-nicotinamide;

3-(3-{4-[(3-hydroxy-benzoylamino)-methyl]-benzyl carbamoyl}-pyridin-2-yloxy)-benzoic acid ethyl ester;

2-(4-fluoro-phenoxy)-N-{4-[(6-fluoro-2-hydroxy-benzoylamino)-methyl]-benzyl}-nicotinamide;

2-(4-fluoro-phenoxy)-N-{4-[(5-fluoro-2-hydroxy-benzoylamino)-methyl]-benzyl}-nicotinamide;

2-(4-fluoro-phenoxy)-N-{4-[(3-hydroxy-4-methyl-benzoylamino)-methyl]-benzyl}-nicotinamide;

2-(4-fluoro-phenoxy)-N-{4-[(3-hydroxy-benzoylamino)-methyl]-benzyl}-nicotinamide;

2-(4-fluoro-phenoxy)-N-{4-[(2-hydroxy-benzoylamino)-methyl]-benzyl}-nicotinamide;

2-(4-fluoro-phenoxy)-N-{4-[(4-hydroxy-benzoylamino)-methyl]-benzyl}-nicotinamide;

2-(4-fluoro-phenoxy)-N-{4-[(2-hydroxy-4-methyl-benzoylamino)-methyl]-benzyl}-nicotinamide;

2-(4-fluoro-phenoxy)-N-{4-[(3-hydroxy-2-methyl-benzoylamino)-methyl]-benzyl}nicotinamide;

2-(4-fluoro-phenoxy)-N-{4-[(2-hydroxy-5-methyl-benzoylamino)-methyl]-benzyl}nicotinamide;

5-fluoro-2-(4-fluoro-phenoxy)-N-{4-[(2-hydroxy-benzoylamino)-methyl]-benzyl}-nicotinamide;
5-fluoro-2-(4-fluoro-phenoxy)-N-{4-[(2-hydroxy-acetyl-amino)-methyl]-benzyl}-nicotinamide;
5-fluoro-2-(4-fluoro-phenoxy)-N-{4-[(4-hydroxy-benzoylamino)-methyl]-benzyl}-nicotinamide;
3-(3-{4-[(3-hydroxy-benzoylamino)-methyl]-benzylxarbamoyl}-pyridin-2-yloxy)-benzoic acid ethyl ester;
3-(3-{4-[(2-hydroxy-phenacetyl-amino)-methyl]-benzycarbamoyl}-pyridin-2-yloxy)-benzoic acid ethyl ester;
3-(3-{4-[(3-hydroxy-phenacetyl-amino)-methyl]-benzycarbamoyl}-pyridin-2-yloxy)-benzoic acid ethyl ester; or
3-(3-{4-[(4-hydroxy-phenacetyl-amino)-methyl]-benzycarbamoyl}-pyridin-2-yloxy)-benzoic acid ethyl ester.

6. A process for preparing a compound of claim 1 wherein Y is:

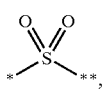
(1.7)

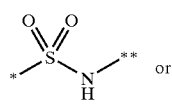
(1.8) or

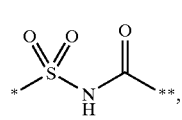
(1.10)

or a pharmaceutically acceptable salt thereof, comprising reacting a compound of formula:

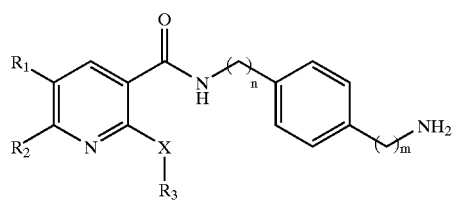
(2)

wherein $R_1$, $R_2$, X. $R_3$, n and m are as defined in claim 1. with the corresponding $R_1$-sulfonyl chloride derivative.

7. A process for preparing a compound of claim 1 wherein Y is:

(1.5)

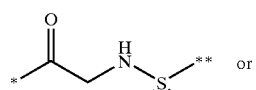
(1.9) or

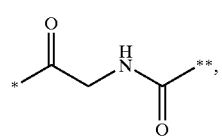
(1.11)

or a pharmaceutically acceptable salt thereof, comprising reacting a compound of formula:

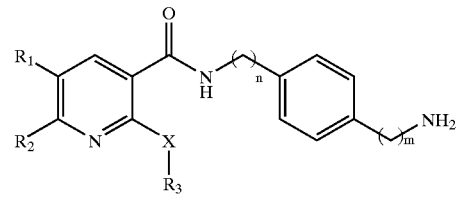
(2)

wherein $R_1$, $R_2$, X, $R_3$, n and m are as defined in claim 1, with the corresponding $R_4$-carboxylic acid derivative.

8. A process for preparing a compound of claim 1 wherein Y is:

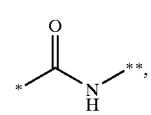
(1.6)

or a pharmaceutically acceptable salt thereof, comprising reacting a compound of formula:

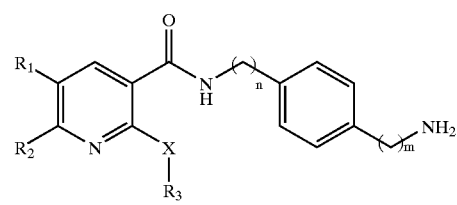
(2)

wherein $R_1$, $R_2$, X, $R_3$, n and m are as defined in claim 1, with carbonyldiimidazole.

9. A pharmaceutical composition comprising a compound of claim 1 or a pharmaceutically acceptable salt thereof and a pharmaceutically acceptable excipient and/or additive.

10. A method of treating a disease, disorder or condition mediated by the PDE4 isozyme in a mammal, said method comprising administering to said mammal in need of such mediation, a therapeutically effective amount of a compound of claim 1 or a pharmaceutically acceptable salt thereof.

11. A method of claim 10 wherein said disease, disorder or condition is asthma.

12. A method of claim 11 wherein said disease, disorder or condition is atopic asthma; non-atopic asthma; allergic asthma; bronchial asthma; essential asthma; true asthma; intrinsic asthma caused by pathophysiologic disturbances; extrinsic asthma caused by environmental factors; essential asthma of unknown or inapparent cause; bronchitic asthma; emphysematous asthma; exercise-induced asthma; occupational asthma; infective asthma caused by bacterial, fungal, protozoal or viral infection; non-allergic asthma; incipient asthma; or wheezy infant syndrome.

13. A method of claim 10 wherein said disease, disorder or condition is chronic or acute bronchoconstriction chronic bronchitis; small airways obstruction; emphysema; pneumoconiosis; chronic eosinophilic pneumonia; chronic obstructive pulmonary disease; adult respiratory distress syndrome; or exacerbation of airways hyper-reactivity consequent to other drug therapy.

14. A method of claim 13 wherein said chronic obstructive pulmonary disease is characterized by irreversible, progressive airways obstruction.

15. A method of claim 13 wherein said pneumonconiosis is aluminosis; bauxite workers' disease; anthracosis; miners' disease; asbestosis; steam-fitter' asthma; chalicosis; flint disease; ptilosis caused by inhaling the dust from ostrich feathers; siderosis caused by the inhalation of iron particles; silicosis; grinders' disease; byssinosis; cotton-dust asthma; or talc pneumoconiosis.

16. A method of claim 10 wherein said disease, disorder or condition is bronchitis; acute bronchitis; chronic bronchitis; acute laryngotracheal bronchitis; arachidic bronchitis; catarrhal bronchitis; croupus bronchitis; dry bronchitis; infectious asthmatic bronchitis; productive bronchitis; staphylococcus bronchitis; streptococcal bronchitis; or vesicular bronchitis.

17. A method of claim 10 wherein said disease, disorder or condition is bronchiectasis, cylindric bronchiectasis; sacculated bronchiectasis; fusiform brochiectasis; capillary bronchiectasis; cystic bronchiectasis; dry bronchiectass or follicular bronchiectasis.

18. A method of claim 10 wherein said disease, disorder or condition is seasonal allergic rhinitis; perennial allergic rhinitis; sinusitis; purulent sinusitis; nonpurulent sinusitis; acute sinusitis; chronic sinusitis; ethmoid sinusitis; frontal sinusitis; or sphenoid sinusitis.

19. A method of claim 10 wherein said disease, disorder or condition is regulated by the activation and degranulation of eosinophils.

20. A method of any one of claims 10–19 wherein said compound or pharmaceutically acceptable salt thereof is administered together with a pharmaceutically acceptable excipient and/or additive.

* * * * *